(12) United States Patent
Miki et al.

(10) Patent No.: US 11,931,004 B2
(45) Date of Patent: Mar. 19, 2024

(54) OBJECTIVE OPTICAL SYSTEM

(71) Applicant: OLYMPUS CORPORATION, Tokyo (JP)

(72) Inventors: Takehiro Miki, Tokyo (JP); Keiichiro Nakajima, Tokyo (JP); Mitsuru Namiki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 501 days.

(21) Appl. No.: 17/137,574

(22) Filed: Dec. 30, 2020

(65) Prior Publication Data

US 2021/0145253 A1 May 20, 2021

Related U.S. Application Data

(63) Continuation of application No. PCT/JP2018/025647, filed on Jul. 6, 2018.

(51) Int. Cl.
*A61B 1/00* (2006.01)
*G02B 9/06* (2006.01)
(Continued)

(52) U.S. Cl.
CPC ........ *A61B 1/0019* (2013.01); *A61B 1/00195* (2013.01); *G02B 9/06* (2013.01); *G02B 9/58* (2013.01); *G02B 23/243* (2013.01)

(58) Field of Classification Search
CPC .... A61B 1/0019; A61B 1/00195; G02B 9/06; G02B 9/58; G02B 23/243; G02B 13/004
See application file for complete search history.

(56) References Cited

U.S. PATENT DOCUMENTS 2,783,757 A * 3/1957 Scholz ............... A61B 1/00096
600/176
3,930,729 A * 1/1976 Gunn ................. G01B 9/02097
356/450
(Continued)

FOREIGN PATENT DOCUMENTS

CN 206710686 * 12/2017
JP S56-149009 A 11/1981
(Continued)

OTHER PUBLICATIONS

Japanese Office Action dated Nov. 2, 2021 received in 2020-528642.
(Continued)

*Primary Examiner* — Wyatt A Stoffa
*Assistant Examiner* — Ray Alexander Dean
(74) *Attorney, Agent, or Firm* — Scully, Scott, Murphy & Presser, P.C.

(57) ABSTRACT

Provided is an objective optical system including: a first spherical lens and a second spherical lens that are arrayed in this order from an object; and at least one of a first optical medium and a second optical medium, wherein the first optical medium is a solid or liquid disposed at an object side of the first spherical lens and is in close contact with a surface on the object side of the first spherical lens, over an entire optical path; and the second optical medium is a solid or liquid disposed at an opposite side of the second spherical lens from the object and is in close contact with a surface on the opposite side of the second spherical lens from the object, over the entire optical path.

18 Claims, 22 Drawing Sheets

(51) Int. Cl.
 *G02B 9/58* (2006.01)
 *G02B 23/24* (2006.01)

(56) References Cited

U.S. PATENT DOCUMENTS

| | | | | |
|---|---|---|---|---|
| 4,557,566 | A * | 12/1985 | Kikuchi | G02B 3/0087 359/652 |
| 4,848,882 | A * | 7/1989 | Suzuki | G02B 6/425 385/33 |
| 6,288,845 | B1 * | 9/2001 | Harada | G02B 7/023 396/448 |
| 6,594,086 | B1 * | 7/2003 | Pakdaman | G11B 7/1387 359/368 |
| 2003/0233029 | A1 | 12/2003 | Alekseenko et al. | |
| 2004/0133071 | A1 | 7/2004 | Alekseenko et al. | |
| 2006/0056040 | A1 * | 3/2006 | Lan | G02B 6/06 359/664 |
| 2009/0287057 | A1 | 11/2009 | Murata et al. | |
| 2013/0258490 | A1 | 10/2013 | Ishihara | |
| 2015/0309285 | A1 | 10/2015 | Ishihara | |

FOREIGN PATENT DOCUMENTS

| | | |
|---|---|---|
| JP | S57-35808 A | 2/1982 |
| JP | S63-023118 A | 1/1988 |
| JP | 2005-528182 A | 9/2005 |
| JP | 2007-515211 A | 6/2007 |
| JP | 2009-276502 A | 11/2009 |
| JP | 2010-236870 A | 10/2010 |
| JP | 2013-210543 A | 10/2013 |
| JP | 2015-118136 A | 6/2015 |
| WO | 2003/103482 A1 | 12/2003 |
| WO | 2005/053519 A1 | 6/2005 |
| WO | WO-2012162209 A1 * 11/2012 ............... G02B 3/00 |

OTHER PUBLICATIONS

International Search Report dated Oct. 9, 2018 issued in PCT/JP2018/025647.

* cited by examiner

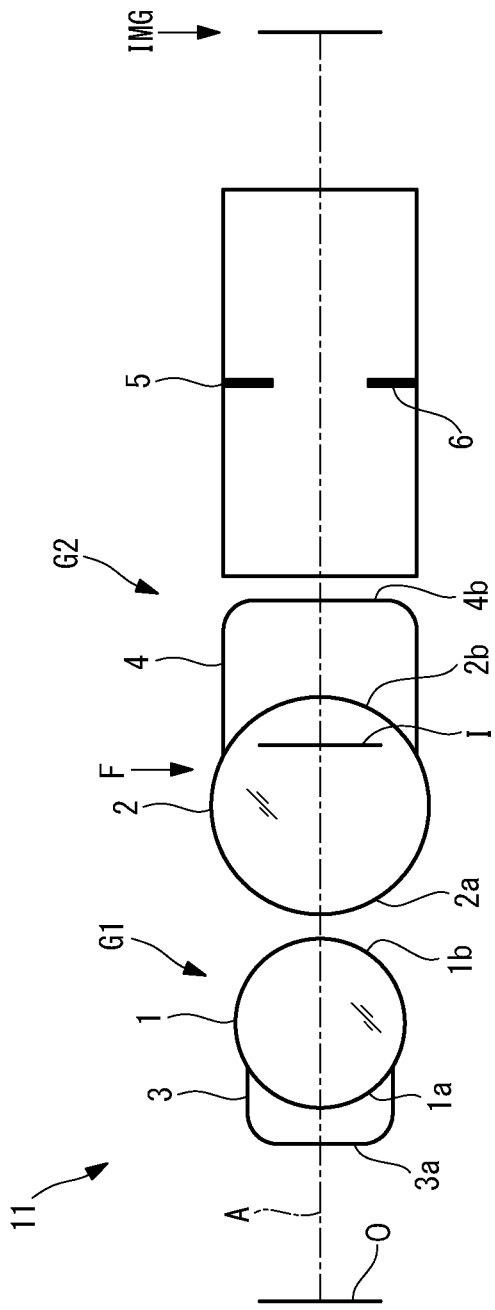

US 11,931,004 B2

OBJECTIVE OPTICAL SYSTEM

CROSS-REFERENCE TO RELATED APPLICATIONS

This is a continuation of International Application PCT/JP2018/025647, with an international filing date of Jul. 6, 2018, which is hereby incorporated by reference herein in its entirety.

TECHNICAL FIELD

The present invention relates to an objective optical system.

BACKGROUND ART

In the related art, there is a known objective optical system that includes a spherical lens (for example, see PTL 1). A spherical lens has a simple shape, thus facilitating manufacturing, assembly, and minimization. Therefore, a spherical lens is suitable for an objective optical system in a small-diameter endoscope.

CITATION LIST

Patent Literature

{PTL 1} Japanese Translation of PCT International Application, Publication No. 2007-515211

SUMMARY OF INVENTION

According to one aspect, the present invention provides an objective optical system including: a first spherical lens and a second spherical lens that are arrayed in this order from an object; and at least one of a first optical medium and a second optical medium, wherein the first optical medium is a solid or liquid disposed at an object side of the first spherical lens and is in close contact with a surface on the object side of the first spherical lens, over an entire optical path; and the second optical medium is a solid or liquid disposed at an opposite side of the second spherical lens from the object and is in close contact with a surface on the opposite side of the second spherical lens from the object, over the entire optical path.

BRIEF DESCRIPTION OF DRAWINGS

FIG. 3 is a view of the overall configuration of still another modification of the objective optical system shown in FIG. 1.

DESCRIPTION OF EMBODIMENTS

An objective optical system according to one embodiment of the present invention will be described below with reference to the drawings.

Figure 1:
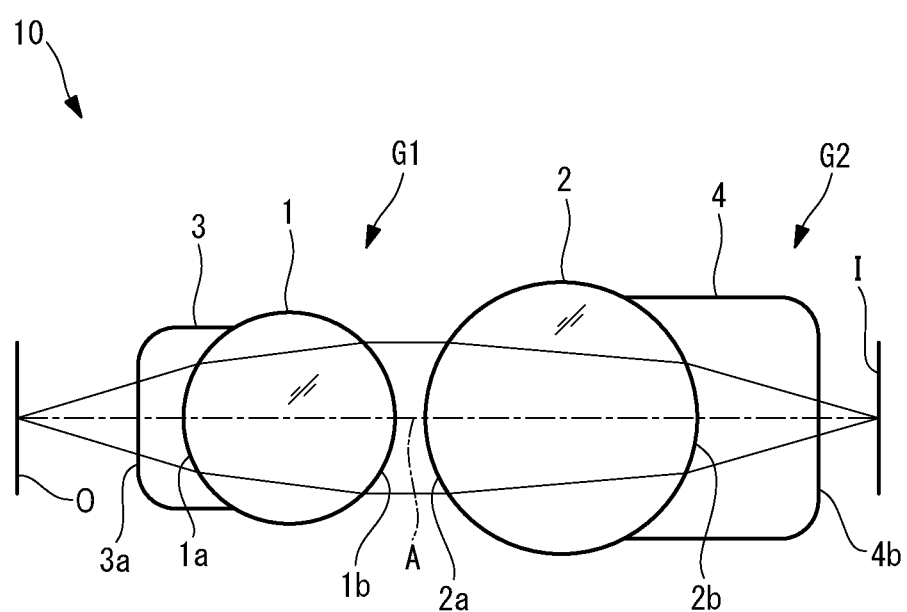
FIG. 1 is a view of the overall configuration of an objective optical system according to one embodiment of the present invention.

As shown in FIG. 1, an objective optical system 10 of this embodiment includes a first group G1 and a second group G2 that are arrayed on an optical axis A in this order from an object O. The objective optical system 10 may further include an optical element that practically does not have refractive power, such as a cover glass or a filter.

The first group G1 includes a first spherical lens 1 and a first optical medium 3.

The first spherical lens 1 has a lens surface 1a on the object O side and a lens surface 1b on the opposite side from the object O. The lens surface 1a and the lens surface 1b are spherical surfaces that have radii of curvature identical to each other and that have a common center of curvature.

The first optical medium 3 is disposed at the object O side of the first spherical lens 1. The first optical medium 3 is in close contact with the lens surface 1a, over the entire optical path on the lens surface 1a, through which light from the object O passes. A surface (object-side surface) 3a on the object O side of the first optical medium 3 is a flat surface or a spherical surface that has an arbitrary curvature.

The second group G2 includes a second spherical lens 2 and a second optical medium 4.

The second spherical lens 2 has a lens surface 2a on the object O side and a lens surface 2b on the opposite side from the object O. The lens surface 2a and the lens surface 2b are spherical surfaces that have radii of curvature identical to each other and that have a common center of curvature.

The second optical medium 4 is disposed at the opposite side of the second spherical lens 2 from the object O. The second optical medium 4 is in close contact with the lens surface 2b, over the entire optical path on the lens surface 2b, through which light from the object O passes. A surface (image-side surface) 4b of the second optical medium 4 on the opposite side from the object O is a flat surface or a spherical surface that has an arbitrary curvature.

The optical path between the lens surface 1b and the lens surface 2a is filled with air. The lens surface 1b and the lens surface 2a may be in contact with each other at one point on the optical axis A or may be apart from each other.

Light from the object O forms an image by being transmitted through the first optical medium 3, the first spherical lens 1, the second spherical lens 2, and the second optical medium 4. At this time, the image formation position might be located inside the second spherical lens 2 or the second optical medium 4, in some cases. In those cases, a luminous flux after the image formation is transmitted through the second spherical lens 2 and the second optical medium 4 or is transmitted through the second optical medium 4. A back focal point of the objective optical system 10 (a back focal point of the whole of the first group G1 and the second group G2) is located at the opposite side of the lens surface 2a from the object O. The back focal point is the image formation position when a parallel luminous flux enters the lens system.

The first optical medium 3 and the second optical medium 4 are each an optically transparent liquid or an optically transparent solid. The liquid is, for example, water or oil. The solid is, for example, plastic, glass, or a coating material. The optical media 3 and 4 each have a refractive index larger than the refractive index of air. From the point of view of the ease of manufacture of each of the first group G1 and the second group G2, it is preferred that the optical media 3 and 4 be an optical adhesive or resin. For example, the optical media 3 and 4 are formed by hardening a general-purpose optical adhesive on the lens surfaces 1a and 2b, respectively.

Next, the operation of the thus-configured objective optical system 10 will be described below.

The first spherical lens 1 and the second spherical lens 2 each have positive refractive power. Therefore, light from the object O entering the objective optical system 10 can be focused by the first spherical lens 1 and the second spherical lens 2 and can be formed into an image I of the object O.

In this case, because the manufacturing technology for bearing steel balls can be applied to manufacture the spherical lenses 1 and 2, it is easy to manufacture and minimize the spherical lenses 1 and 2. Furthermore, because the spherical lenses 1 and 2 are spheres, the assembly is easy. Therefore, there is an advantage in that it is possible to easily manufacture the small objective optical system 10, which is suitable for being mounted in a distal-end section of a small-diameter endoscope, for example.

Furthermore, with the first optical medium 3, which is in close contact with the lens surface 1a, the angle of refraction of a light ray at the lens surface 1a is reduced compared with a case in which the first optical medium 3 is not provided. Similarly, with the second optical medium 4, which is in close contact with the lens surface 2b, the angle of refraction of a light ray at the lens surface 2b is reduced compared with a case in which the second optical medium 4 is not provided. Accordingly, there is an advantage in that it is possible to suppress the amount of aberration occurring due to the spherical lenses 1 and 2 and to form a smaller-aberration high-quality image I by using the spherical lenses 1 and 2.

Furthermore, by providing the optical medium 3, the positive refractive power of the first group G1 is weakened compared with the positive refractive power of the single spherical lens 1. Similarly, by providing the optical medium 4, the positive refractive power of the second group G2 is weakened compared with the positive refractive power of the single spherical lens 2. According to this embodiment, by using the two spherical lenses 1 and 2, it is possible to compensate for the weakening of the refractive power due to the optical media 3 and 4 and to realize a positive refractive power equal to or greater than the positive refractive power of the single spherical lens 1 or 2.

Furthermore, there is an advantage in that it is possible to secure an angle of view equal to or greater than the angle of view of an objective optical system that is formed of a single spherical lens, by providing the two spherical lenses 1 and 2. For example, the angle of view of an objective optical system that consists of only the spherical lens 2 and the optical medium 4 is less compared with the angle of view of an objective optical system that consists of only the spherical lens 2. The two spherical lenses 1 and 2 can make up for such a reduction of the angle of view due to the optical media 3 and 4.

Note that, in this specification, a "spherical lens" is a lens in which a lens surface on the object side and a lens surface on the opposite side from the object are spherical surfaces that have radii of curvature identical to each other and that have a common center of curvature. Therefore, a "spherical lens" includes a lens in which a surface other than the two lens surfaces on the object side and the opposite side from the object has a shape other than a spherical surface.

Figure 2A:
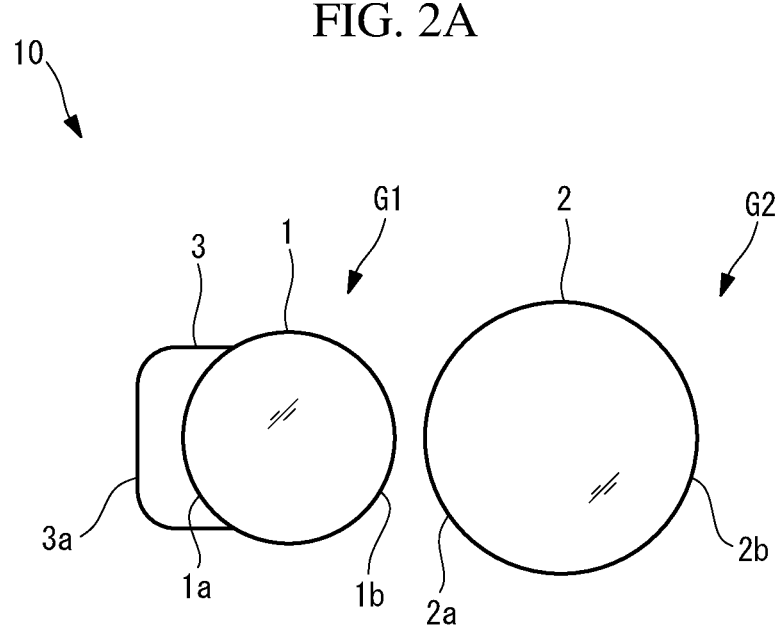
FIG. 2A is a view of the overall configuration of a modification of the objective optical system shown in FIG. 1.
Figure 2B:
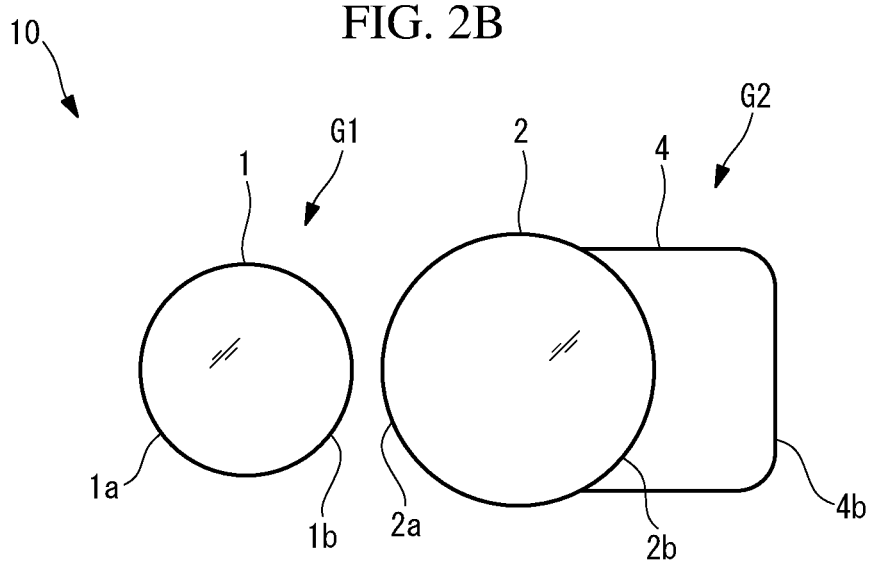
FIG. 2B is a view of the overall configuration of another modification of the objective optical system shown in FIG. 1.

In this embodiment, although the first optical medium 3 and the second optical medium 4 are both provided, instead of this, as shown in FIGS. 2A and 2B, only one of the first optical medium 3 and the second optical medium 4 may be provided.

With a configuration in which one of the optical media 3 and 4 is omitted, it is possible to obtain the effect of reduction of the angle of refraction of a light ray at the lens surface 1a or the lens surface 2b. Therefore, with the two spherical lenses 1 and 2 and the one optical medium 3 or 4, it is possible to balance both: large refractive power and angle of view; and suppression of the occurrence of aberration.

In this embodiment, as shown in FIG. 3, it is also possible to further include an image transmission system 5 that is disposed at the opposite side of the second spherical lens 2 from the object O and that transmits an image I formed by the first and second spherical lenses 1 and 2.

The image transmission system 5 is a combination of a plurality of lenses or a gradient index (GRIN) lens. By providing the image transmission system 5, an image I formed by the first group G1 and the second group G2 can be re-imaged in an image plane IMG at a desired position.

In an objective optical system 11 that includes the image transmission system 5, it is preferred that a back focal point F be located inside the second spherical lens 2, as shown in FIG. 3. In a design in which the back focal point F is located inside the second spherical lens 2, negative refractive power of the object-side surface 3a and the lens surface 1a is reduced, and the maximum ray height of a marginal ray of each luminous flux is lowered compared with a design in which the back focal point F is located at the opposite side of the second spherical lens 2 from the object O. Therefore, the spherical aberration and the chromatic aberration can be further reduced. Furthermore, in a case in which the back focal point matches the optical surfaces 1a, 1b, 2a, or 2b of the spherical lens 1 or 2 or the optical surface 3a or 4b of the optical medium 3 or 4, dust etc. on the optical surface affects an object image at infinity formed by the first and second spherical lenses 1 and 2, thus causing deterioration of the quality of the object image at infinity. When the back focal point F is located inside the second spherical lens 2, the focus is not set at dust etc. on the optical surface 1a, 1b, 2a, 2b, 3a, or 4b in the optical path, thus making it possible to prevent deterioration of the quality of an object image at infinity caused by the dust etc.

In a case in which the first spherical lens 1 and the second spherical lens 2 have radii identical to each other and are made of materials identical to each other, and the object-side surface 3a of the first optical medium 3 is a flat surface perpendicular to the optical axis A, the objective optical system 11 satisfies the following conditional expression (1):

$$0 \leq \{n_1(2n_3-n_1)-n_1LN\}/\{2n_3-(n_1-3n_3)(n_1-2)-(n_1-1)LN\} \leq 2 \quad (1)$$

where $n_1$ indicates the refractive index of the first and second spherical lenses 1 and 2, $R_1$ indicates the radius of the first and second spherical lenses 1 and 2, $n_3$ indicates the refractive index of the first optical medium 3, and L indicates the interval on the optical axis A between the lens surface 1b and the lens surface 2a. Here, $N=(n_1n_3+n_1-2n_3)/R_1$.

Conditional expression (1) defines a condition for the back focal point F to be located inside the second spherical lens 2. Specifically, design is carried out so as to satisfy conditional expression (1), thereby making it possible to manufacture the objective optical system 11, in which the back focal point F is located inside the second spherical lens 2.

In a case in which the lens surface 1b and the lens surface 2a are in contact with each other on the optical axis A (i.e., L=0), conditional expression (1) is rewritten as in the following conditional expression (1'):

$$0 \leq \{n_1(2n_3-n_1)\}/\{2n_3-(n_1-3n_3)(n_1-2)\} \leq 2 \quad (1')$$

In a case in which the back focal point F is located inside the second spherical lens 2, and the image-side surface 4b is a flat surface perpendicular to the optical axis A, the objective optical system 11 may satisfy the following conditional expression (2):

$$1 \leq (R_1+R_2)*[\{1/\cos(2\theta_2-\theta_1)\}-1]/L \quad (2)$$

where $R_1$ indicates the radius of the first spherical lens 1, $R_2$ indicates the radius of the second spherical lens 2, L indicates the interval on the optical axis A between the lens surface 1b and the lens surface 2a, $n_2$ indicates the refractive index of the second spherical lens 2, and $n_4$ indicates the refractive index of the second optical medium 4. Here, $\theta_1=\sin^{-1}(1/n_4)$, and $\theta_2=\sin^{-1}(1/n_2)$.

Conditional expression (2) defines a condition for a light ray at the maximum image height and parallel to the optical axis A to pass through the first group G1 and the second group G2 without being subjected to vignetting. Specifically, by satisfying conditional expression (2), it is possible to prevent the occurrence of vignetting at the first group G1 and the second group G2 and to secure a field of view as large as possible.

In this embodiment, the objective optical systems 10 and 11 may further include an aperture diaphragm 6 at an arbitrary position in the optical path. With the aperture diaphragm 6, the brightness of an object image I can be appropriately controlled.

The aperture diaphragm 6 is preferably disposed at the opposite side of the second group G2 from the object O and, as shown in FIG. 3, for example, is disposed inside the image transmission system 5.

Figure 4A:
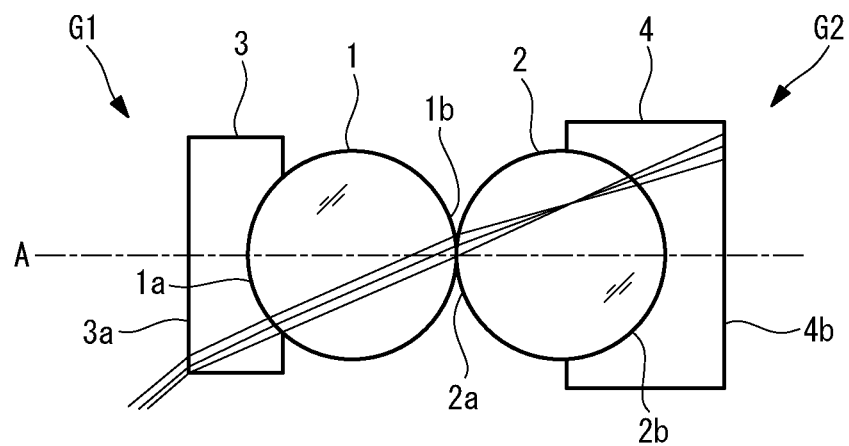
FIG. 4A is a view showing off-axis light in which the chief ray is directed outward at an emission surface of a second group.
Figure 4B:
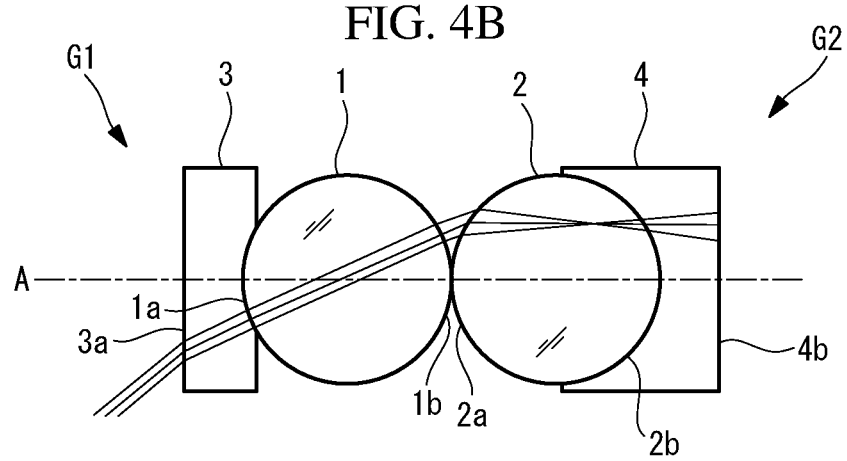
FIG. 4B is a view showing off-axis light in which the chief ray is telecentric at the emission surface of the second group.

The amount of aberration occurring depends on the tilt angle of the chief ray of the outermost off-axis light at the lens surface 2b of the second spherical lens 2 with respect to the optical axis. This tilt angle is controlled by the position of the aperture diaphragm 6 in the objective optical systems 10 and 11. As shown in FIGS. 4A and 4B, the aperture diaphragm 6 is disposed at such a position that the chief ray of off-axis light at the light-ray emission surface (the lens surface 2b or the image-side surface 4b) of the second group G2 is directed outward, is telecentric, or is substantially telecentric.

Figure 4C:
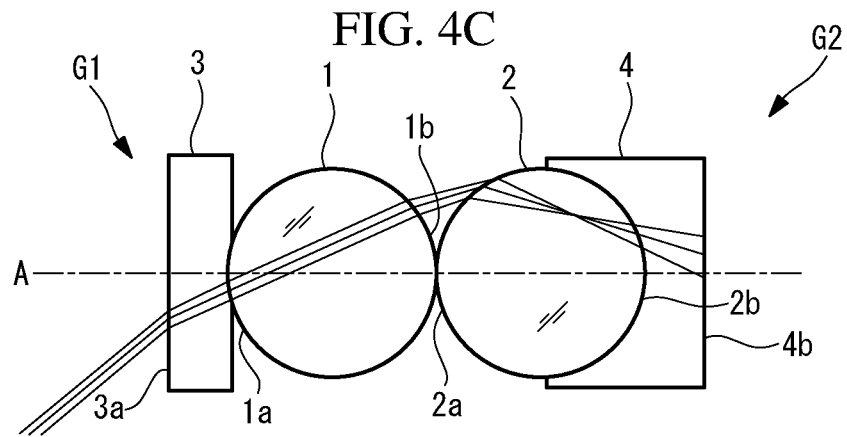
FIG. 4C is a view showing off-axis light in which the chief ray is directed inward at the emission surface of the second group.

Specifically, the aperture diaphragm 6 is disposed at a position at which the chief-ray tilt angle θ becomes 5° or less. The chief-ray tilt angle θ is the tilt angle of the chief ray of the outermost off-axis light with respect to the optical axis A. A positive chief-ray tilt angle θ means that the chief ray of the outermost off-axis light is directed outward (see FIG. 4A), and a negative chief-ray tilt angle θ means that the chief ray of the outermost off-axis light is directed inward (see FIG. 4C).

Figure 5:
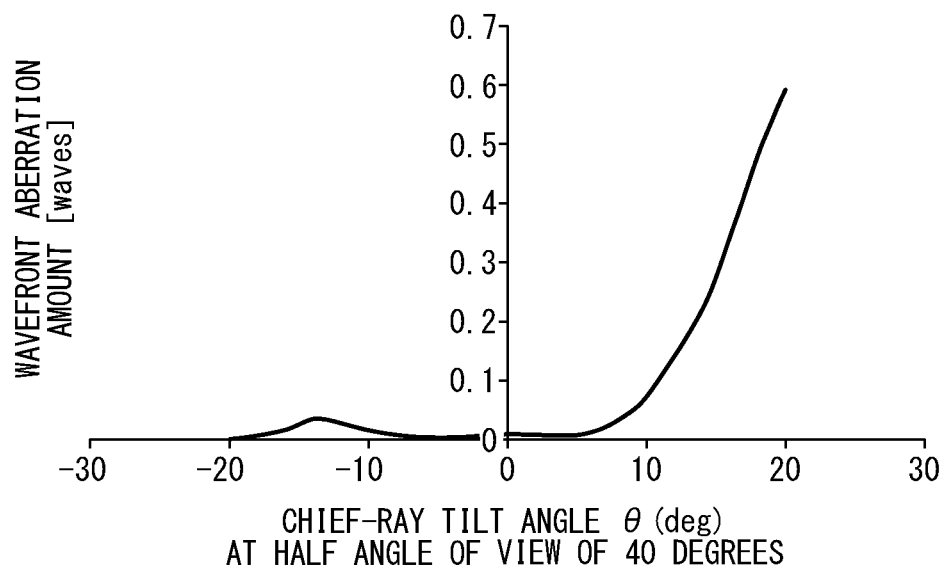
FIG. 5 is a graph showing the relationship between a chief-ray tilt angle and aberrations, obtained through optical simulation.

FIG. 5 shows the result of analysis of the relationship between the chief-ray tilt angle θ and the aberration in an objective optical system of Example 5, to be described later, through optical simulation. Wavefront aberration almost never occurs in a range of θ≤5°. On the other hand, in a range of θ>5°, wavefront aberration is increased as the chief-ray tilt angle θ becomes larger.

In this way, the chief-ray tilt angle θ is controlled so as to become 5° or less by the position of the aperture diaphragm 6, which is disposed at the opposite side of the second group G2 from the object O, thereby making it possible to further suppress the occurrence of aberration.

The objective optical systems 10 and 11 that each include the aperture diaphragm 6 can be suitably combined with an image-acquisition device. The image-acquisition device is disposed, for example, at the opposite side of the image transmission system 5 from the object O. With the aperture diaphragm 6, the brightness of an image I acquired by the image-acquisition device can be appropriately adjusted. Instead of the image-acquisition device, an arbitrary element, such as a lens, aperture, or mirror frame, may be disposed at the opposite side of the image transmission system 5 from the object O.

Next, methods for deriving conditional expressions (1) and (2) will be described below with reference to FIGS. 6 and 7.

Conditional expression (1) is derived as follows.

Figure 6:
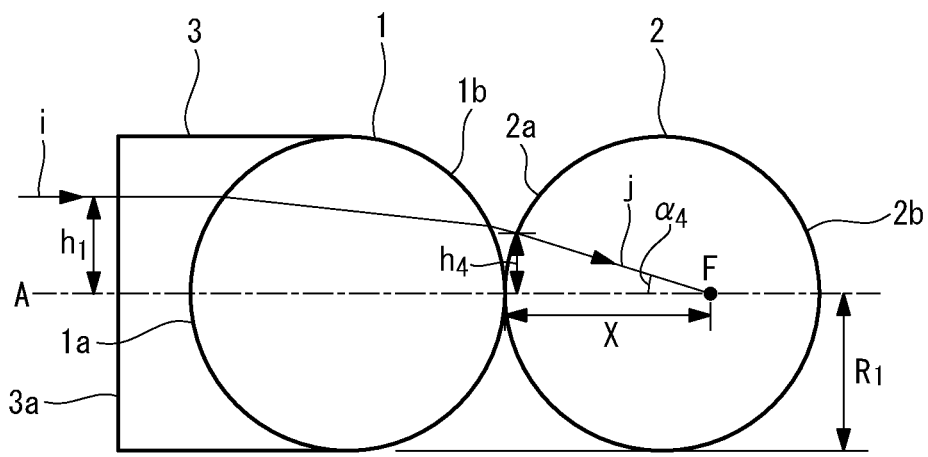
FIG. 6 is a view for explaining a method for deriving a conditional expression (1).

As shown in FIG. 6, paraxial-ray tracing is performed. The back focal point F is located at a position at which a paraxial ray i that has entered parallel to the optical axis A intersects the optical axis A. The fact that the back focal point F is located inside the second spherical lens 2 is equivalent to a paraxial ray j refracted at the lens surface 2a of the second spherical lens 2 intersecting the optical axis A before reaching the lens surface 2b, i.e., the distance X between the lens surface 2a and the back focal point F satisfying the following expression (a):

$$0 \leq X \leq 2 \times R_1 \quad (a)$$

Refraction matrices $R_1$, $R_2$, $R_3$, and $R_4$ at the respective surfaces 3a, 1a, 1b, and 2a and transmission matrices $T_1$, $T_2$, and $T_3$ are as follows.

$$R_1 = \begin{pmatrix} 1 & 0 \\ 0 & 1 \end{pmatrix}, R_2 = \begin{pmatrix} 1 & \frac{n_1 - n_3}{R_1} \\ 0 & 1 \end{pmatrix}, R_3 = \begin{pmatrix} 1 & -\frac{1 - n_1}{R_1} \\ 0 & 1 \end{pmatrix},$$

$$R_4 = \begin{pmatrix} 1 & \frac{n_1 - 1}{R_1} \\ 0 & 1 \end{pmatrix}, T_1 = \begin{pmatrix} 1 & 0 \\ -\frac{d_3}{n_3} & 1 \end{pmatrix}, T_2 = \begin{pmatrix} 1 & 0 \\ -\frac{2R_1}{n_1} & 1 \end{pmatrix},$$

$$T_3 = \begin{pmatrix} 1 & 0 \\ -L & 1 \end{pmatrix}$$

When the paraxial ray i ($h_1$,0) that has entered from the object-side surface 3a turns into the light ray j ($h_4$,$\alpha_4$) by being refracted at the lens surface 2a, the following expression (b) is established.

$$\begin{pmatrix} \alpha_4 \\ h_4 \end{pmatrix} = R_4 T_3 R_3 T_2 R_2 T_1 R_1 \begin{pmatrix} 0 \\ h_1 \end{pmatrix} \quad (b)$$

When $\alpha_4$ and $h_4$ are calculated from expression (b), $X = h_4/(\alpha_4/h_1)$ is obtained. Conditional expression (1) is derived from X and expression (a).

Conditional expression (2) is derived as follows.

Figure 7:
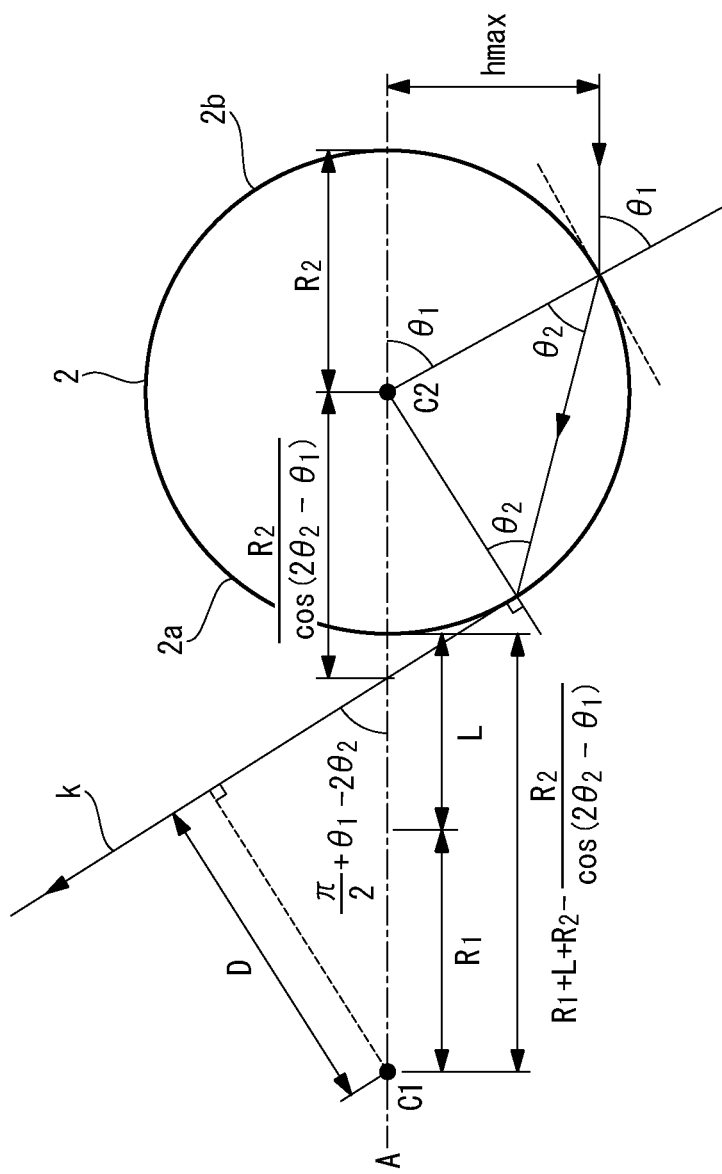
FIG. 7 is a view for explaining a method for deriving a conditional expression (2).

First, as shown in FIG. 7, $h_{max}$ is calculated from a condition for a light ray k traveling from the image I toward the object O to pass through the lens surface 2a. In FIG. 7, reference sign C1 denotes the center of the first spherical lens 1, and reference sign C2 denotes the center of the second spherical lens 2.

In order for the light ray k to pass through the lens surface 2a, the following expression needs to be satisfied based on Snell's law:

$$n_2 \sin \theta_2 \leq 1 \quad (c)$$

Furthermore, the following expression (d) is established from Snell's law at the lens surface 2b:

$$n_4 \sin \theta_1 = n_2 \sin \theta_2 \quad (d)$$

Here, $$\sin \theta_1 = h/R_2 \quad (e).$$

From to expressions (c), (d), and (e), $1 \leq R_2/hn_4$ is obtained, and $h_{max} = R_2/h_4$ is calculated therefrom.

Next, a condition for a light ray that has passed through the edge of the lens surface 2a to intersect the first spherical lens 1 will be considered. This condition is substantially equivalent to a condition for a light ray that has passed through the edge of the lens surface 2a to pass through the first spherical lens 1 and a substance that has the refractive index $n_3$.

In the above-described condition, D in FIG. 7 satisfies $$D \leq R_1 \quad (f).$$

From the geometric relationship in FIG. 7, D is expressed as in the following expression (g).

$$D = \sin\left(\frac{\pi}{2} + \theta_1 - 2\theta_2\right) \cdot \left[R_1 + L + R_2 - \left(\frac{R_2}{\cos(2\theta_2 - \theta_1)}\right)\right] \quad (g)$$

$$= (R_1 + L + R_2) \cdot \cos(2\theta_2 - \theta_1) - R_2$$

Conditional expression (2) is derived from expression (f) and expression (g). However, the following expression is satisfied from Snell's law at the lens surface 2a and the lens surface 2b:

$$\theta_1 = \sin^{-1}(h_{max}/R_2) = \sin^{-1}(1/n_4)$$

$$\theta_2 = \sin^{-1}(1/n_2)$$

EXAMPLES

Next, Examples of the objective optical systems 10 and 11 according to this embodiment will be described below.

In lens data in each Example, r indicates the radius of curvature (mm), d indicates the intersurface spacing (mm), Nd indicates the refractive index at the d-line, vd indicates the Abbe number at the d-line, OBJ indicates the object plane, IMG indicates the image plane, and S indicates the aperture diaphragm. An aberration diagram of an objective optical system according to each Example shows aberration of an image formed by the first group and the second group.

Example 1

Figure 8:
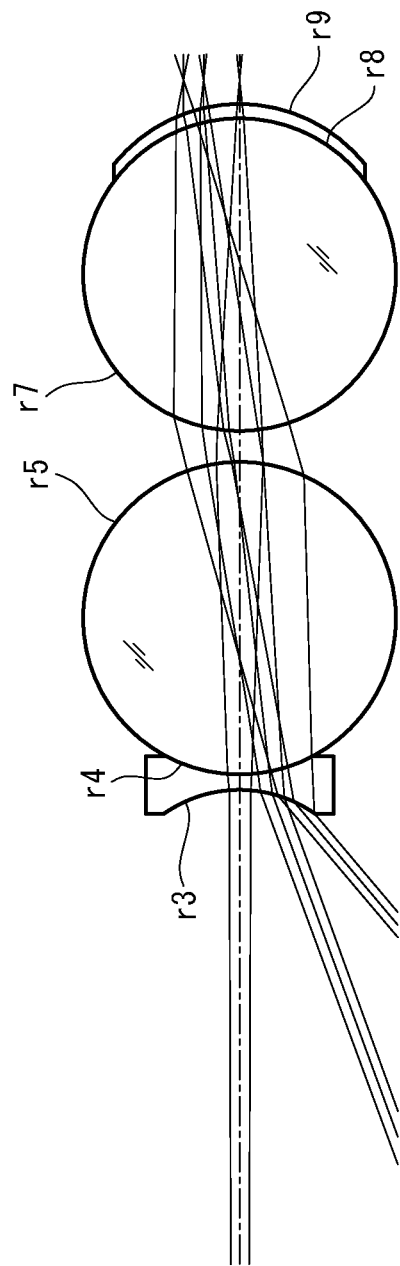
FIG. 8 is a view of the overall configuration of an objective optical system according to Example 1.

FIG. 8 shows the configuration of an objective optical system according to Example 1 of the present invention. The objective optical system of this Example is composed of a first spherical lens, a second spherical lens, a first optical medium, a second optical medium, and an aperture diaphragm. In FIG. 8, the aperture diaphragm is not shown.

Figure 9:
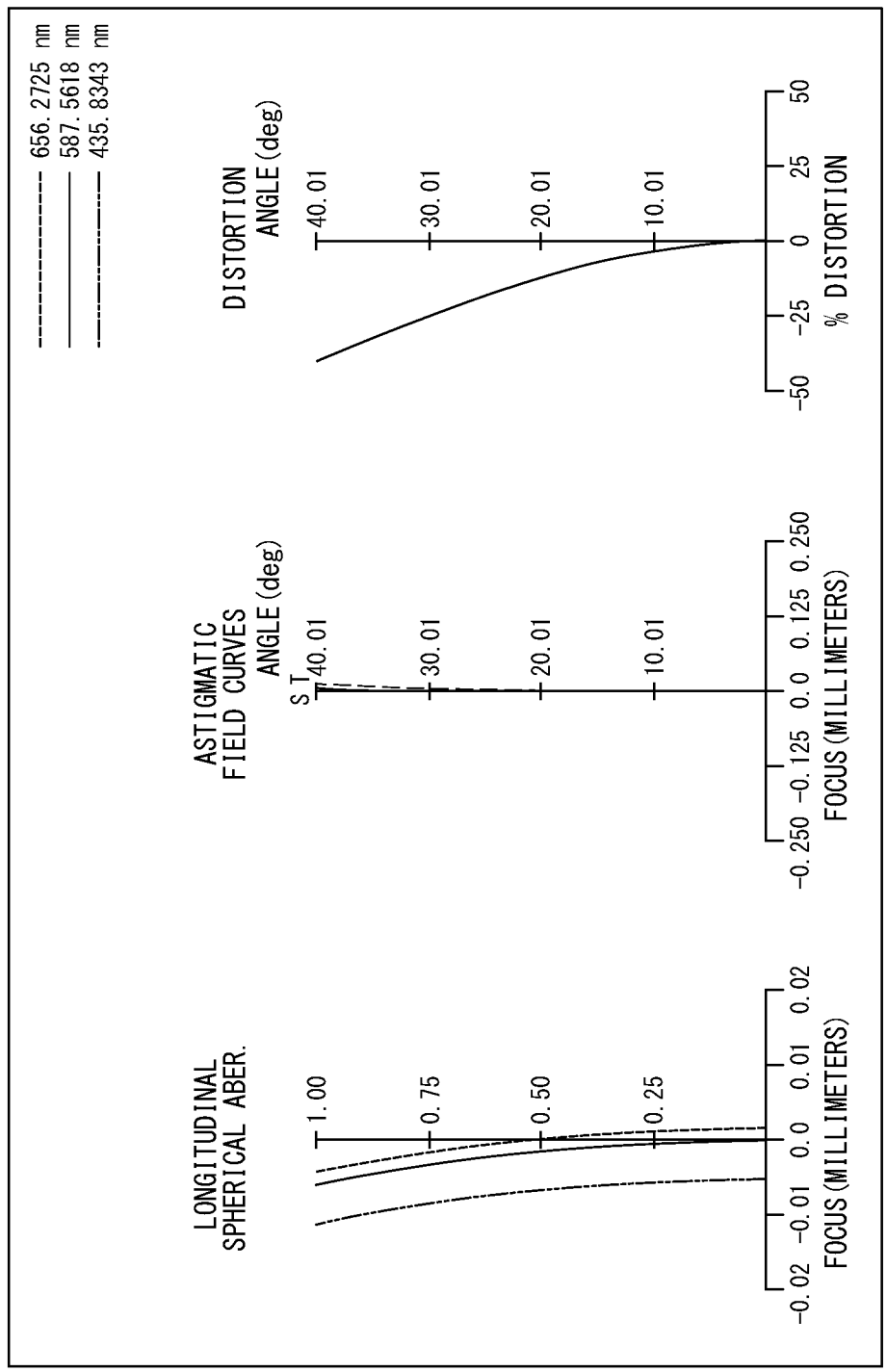
FIG. 9 is an aberration diagram of the objective optical system shown in FIG. 8.

FIG. 9 shows an aberration diagram of the objective optical system of this Example.

| Lens data | | | | |
|---|---|---|---|---|
| Surface number | r | d | Nd | vd |
| OBJ | ∞ | 10 | | |
| 1 | ∞ | 0.0 | | |
| 2 | ∞ | 0.0 | | |
| 3 | −0.41242 | 0.05 | 1.561 | 35.4683 |
| 4 | 0.5 | 1.0 | 1.48749 | 70.4058 |
| 5 | −0.5 | 0.0 | | |
| 6 | ∞ | 0.1 | | |
| 7 | 0.5 | 1.0 | 1.510158 | 58.9349 |
| 8 | −0.5 | 0.05 | 1.561 | 35.4683 |
| 9 | −0.50945 | 0.0 | | |
| 10 | ∞ | 0.2 | | |
| 11 | ∞ | 1000 | | |
| 12S | ∞ | −1000 | | |
| 13 | ∞ | −0.1 | | |
| IMG | ∞ | 0.0 | | |

| Miscellaneous data | |
|---|---|
| Numerical aperture at image side | 0.1 |
| Focal length | 0.35 mm |
| Magnification | −0.034 |
| Half angle of view | 40.0° |
| Image height | 0.18 mm |

Figure 20:
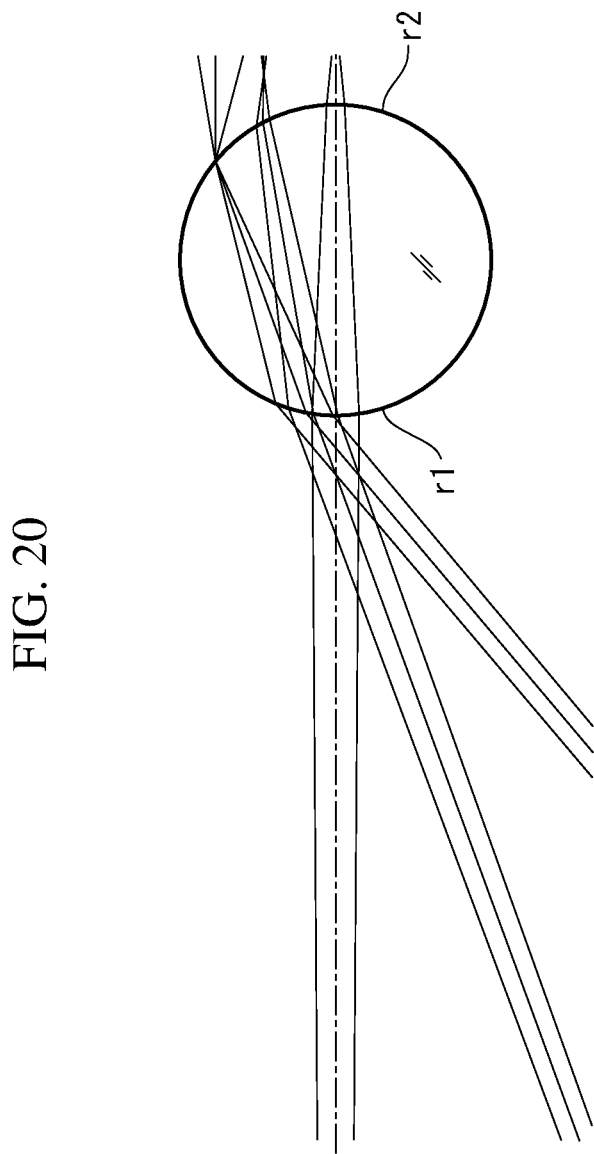
FIG. 20 is a view of the overall configuration of an objective optical system according to Comparative Example 1.
Figure 21:
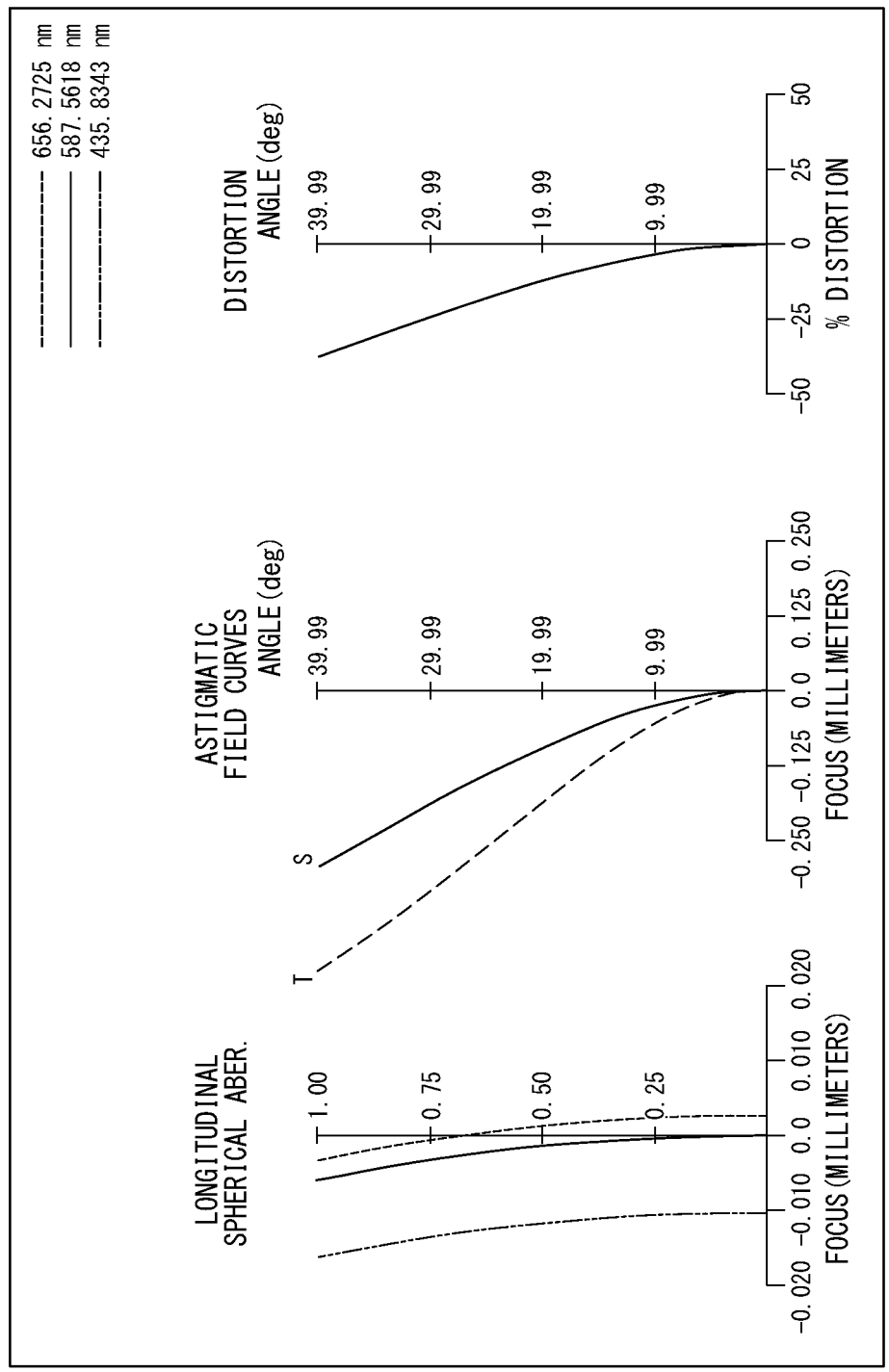
FIG. 21 is an aberration diagram of the objective optical system shown in FIG. 20.

FIG. 20 shows an objective optical system according to Comparative Example 1. The objective optical system of Comparative Example 1 is composed of a single spherical lens and an aperture diaphragm. In FIG. 20, the aperture diaphragm is not shown. The lens data and miscellaneous data of Comparative Example 1 are as follows. FIG. 21 shows an aberration diagram of the objective optical system of Comparative Example 1.

As is clear from comparison between FIG. 9 and FIG. 21, aberration of the objective optical system according to Example 1 of the present invention, specifically, spherical aberration, chromatic aberration, and field curvature thereof, is significantly reduced compared with the aberration in Comparative Example 1.

| Lens data | | | | |
|---|---|---|---|---|
| Surface number | r | d | Nd | vd |
| OBJ | ∞ | 10 | | |
| 1 | 0.5 | 1.0 | 1.5168 | 64.1673 |
| 2 | −0.5 | 0.0 | | |
| 3 | ∞ | 0.0 | | |
| 4 | ∞ | 1000 | | |
| 5S | ∞ | −1000 | | |
| 6 | ∞ | 0.2889 | | |
| IMG | ∞ | 0.0 | | |

| Miscellaneous data | |
|---|---|
| Numerical aperture at image side | 0.1 |
| Focal length | 0.73 mm |
| Magnification | −0.075 |
| Half angle of view | 40.0° |
| Image height | 0.38 mm |

Figure 22:
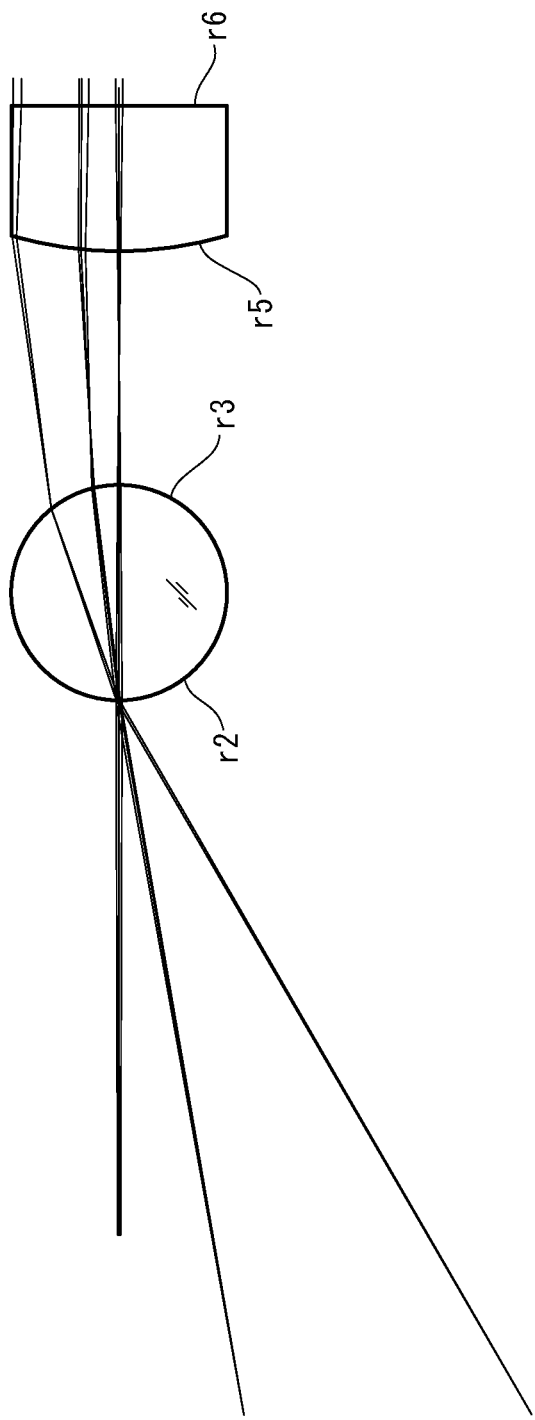
FIG. 22 is a view of the overall configuration of an objective optical system according to Comparative Example 2.
Figure 23:
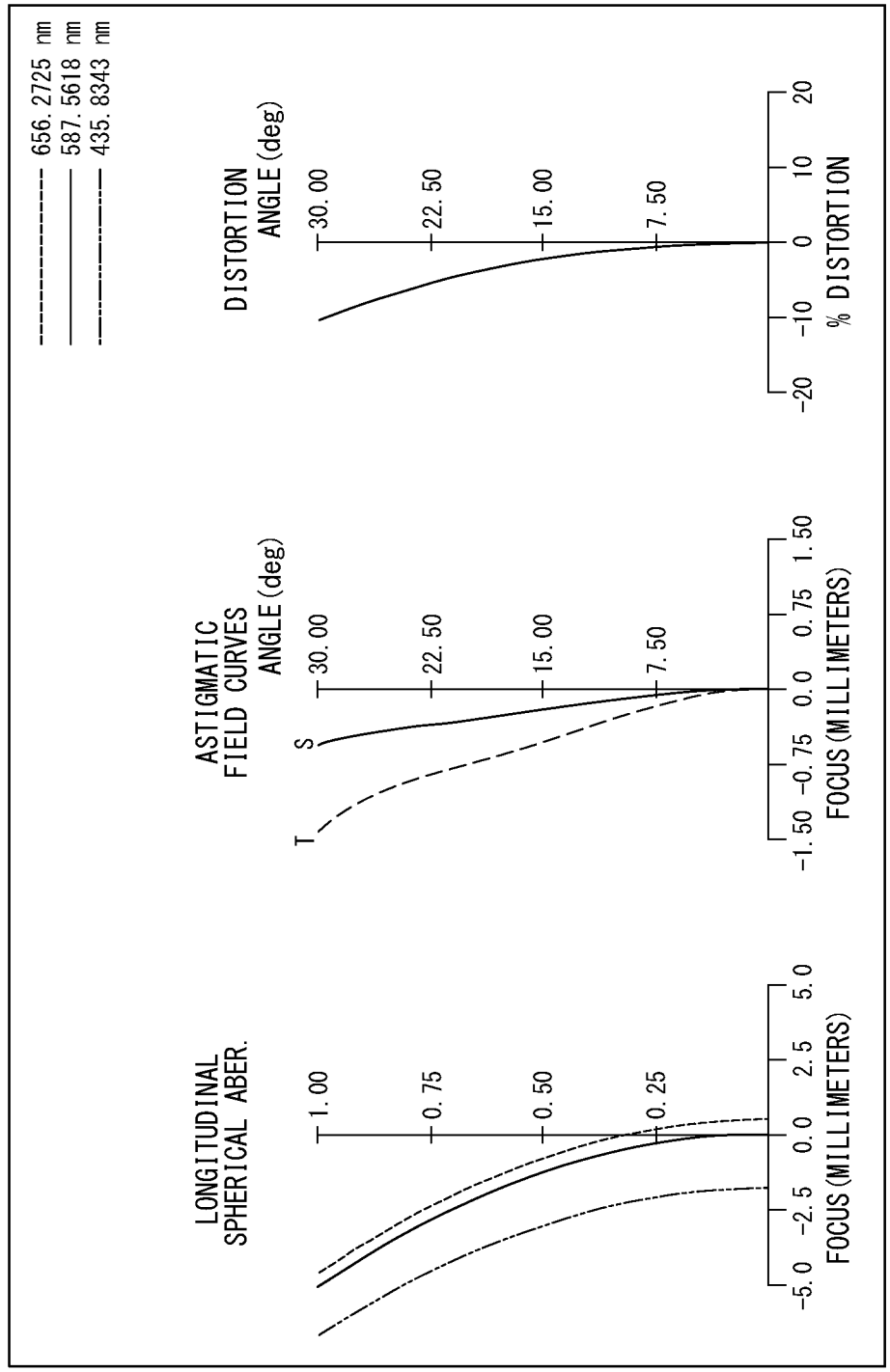
FIG. 23 is an aberration diagram of the objective optical system shown in FIG. 22.

FIG. 22 shows an objective optical system according to Comparative Example 2. The objective optical system of Comparative Example 2 is composed of a single spherical lens, a plano-convex lens, and an aperture diaphragm. The plano-convex lens plays the role of correcting aberration caused by the spherical lens. In FIG. 22, the aperture diaphragm is not shown. Lens data of Comparative Example 2 is as follows, and the numerical aperture at the object side is 0.018. FIG. 23 shows an aberration diagram of the objective optical system of Comparative Example 2.

As is clear from comparison between FIG. 9 and FIG. 23, aberration of the objective optical system according to Example 1 of the present invention, specifically, spherical aberration, chromatic aberration, and field curvature thereof, is significantly reduced compared with the aberration of the objective optical system of Comparative Example 2. Specifically, the effect of suppression of aberration of the spherical lenses due to the first and second optical media is larger than the effect of correction of aberration of the spherical lens due to the plano-convex lens.

| Lens data | | | | |
|---|---|---|---|---|
| Surface number | r | d | Nd | vd |
| OBJ | ∞ | 10 | | |
| 1S | ∞ | 0.0 | | |
| 2 | 1.5 | 3.0 | 1.561 | 35.4683 |
| 3 | −1.5 | 0.0 | | |
| 4 | ∞ | 3.2907 | | |
| 5 | 5.168 | 2.0 | 1.561 | 35.4683 |

| Lens data -continued | | | | |
|---|---|---|---|---|
| Surface number | r | d | Nd | vd |
| 6 | ∞ | 0.0 | | |
| 7 | ∞ | 100 | | |
| 8 | 19.7838 | 2.0 | 1.4927 | 69.82 |
| 9 | ∞ | 63.3977 | | |
| IMG | ∞ | 0.0 | | |

Example 2

Figure 10:
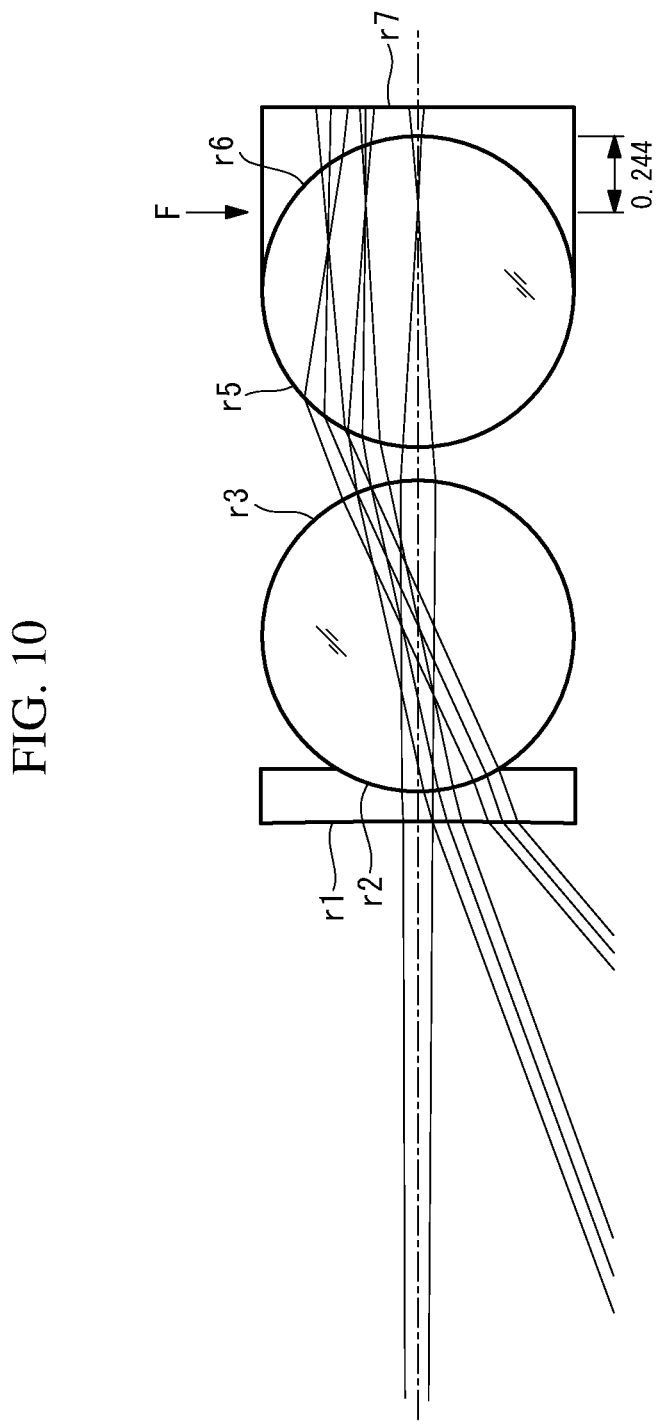
FIG. 10 is a view of the overall configuration of an objective optical system according to Example 2.

FIG. 10 shows the configuration of an objective optical system according to Example 2 of the present invention. The objective optical system of this Example is composed of a first spherical lens, a second spherical lens, a first optical medium, a second optical medium, and an aperture diaphragm. In FIG. 10, the aperture diaphragm is not shown.

The first spherical lens and the second spherical lens have the same radius and are made of the same material. The back focal point F is located inside the second spherical lens. The distance between the back focal point F and the opposite lens surface of the second spherical lens from the object is 0.244 mm.

Figure 11:
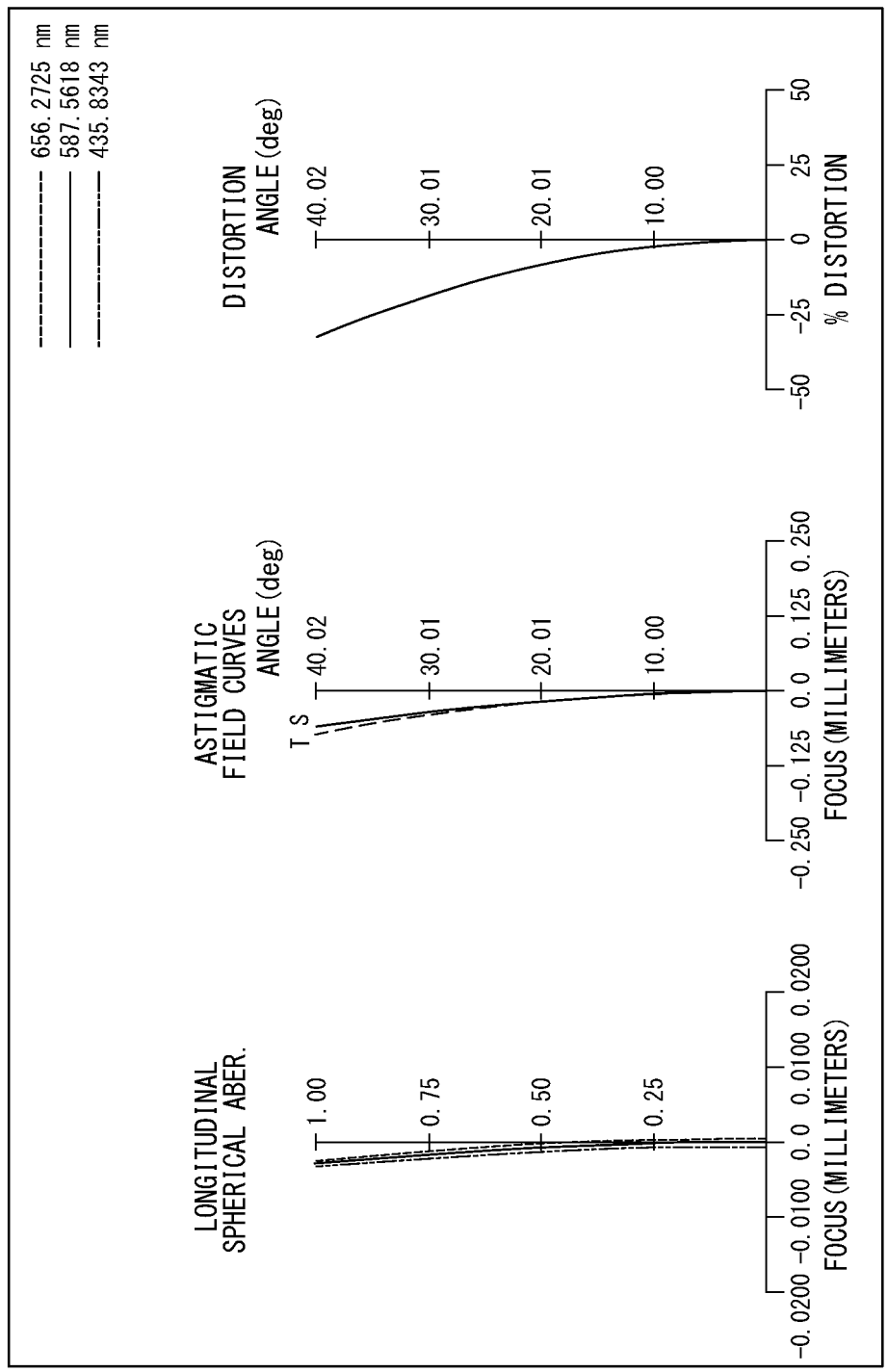
FIG. 11 is an aberration diagram of the objective optical system shown in FIG. 10.

FIG. 11 shows an aberration diagram of the objective optical system of this Example. Compared with Example 1, spherical aberration and chromatic aberration of the objective optical system of this Example are further reduced.

| Lens data | | | | |
|---|---|---|---|---|
| Surface number | r | d | Nd | vd |
| OBJ | ∞ | 10 | | |
| 1 | −7.61988 | 0.1 | 1.561 | 35.4683 |
| 2 | 0.5 | 1.0 | 1.5168 | 64.1673 |
| 3 | −0.5 | 0.0 | | |
| 4 | ∞ | 0.1 | | |
| 5 | 0.5 | 1.0 | 1.5168 | 64.1673 |
| 6 | −0.5 | 0.1 | 1.561 | 35.4683 |
| 7 | ∞ | 1000 | | |
| 8S | ∞ | −1000 | | |
| 9 | ∞ | −0.2 | | |
| IMG | ∞ | 0.0 | | |

| Miscellaneous data | |
|---|---|
| Numerical aperture at image side | 0.1 |
| Focal length | 0.48 mm |
| Magnification | −0.047 |
| Half angle of view | 40.0° |
| Image height | 0.28 mm |

Example 3

Figure 12:
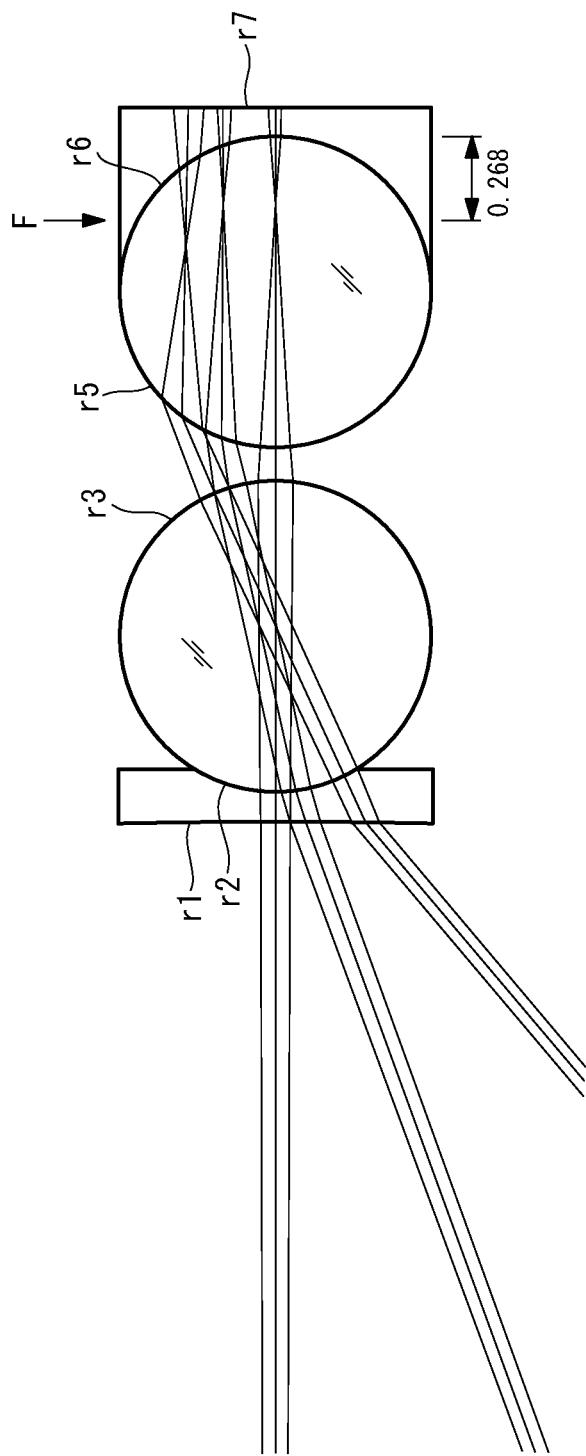
FIG. 12 is a view of the overall configuration of an objective optical system according to Example 3.

FIG. 12 shows the configuration of an objective optical system according to Example 3 of the present invention. The objective optical system of this Example is composed of a first spherical lens, a second spherical lens, a first optical medium, a second optical medium, and an aperture diaphragm. In FIG. 12, the aperture diaphragm is not shown.

The first spherical lens and the second spherical lens have the same radius and are made of the same material. An object-side surface of the first optical medium is a flat surface perpendicular to the optical axis. The back focal point F is located inside the second spherical lens. Specifically, the value of the middle part of the inequality of conditional expression (1) is 1.456, and the objective optical system of this Example satisfies conditional expression (1). The distance between the back focal point F and the opposite lens surface of the second spherical lens from the object is 0.268 mm.

Figure 13:
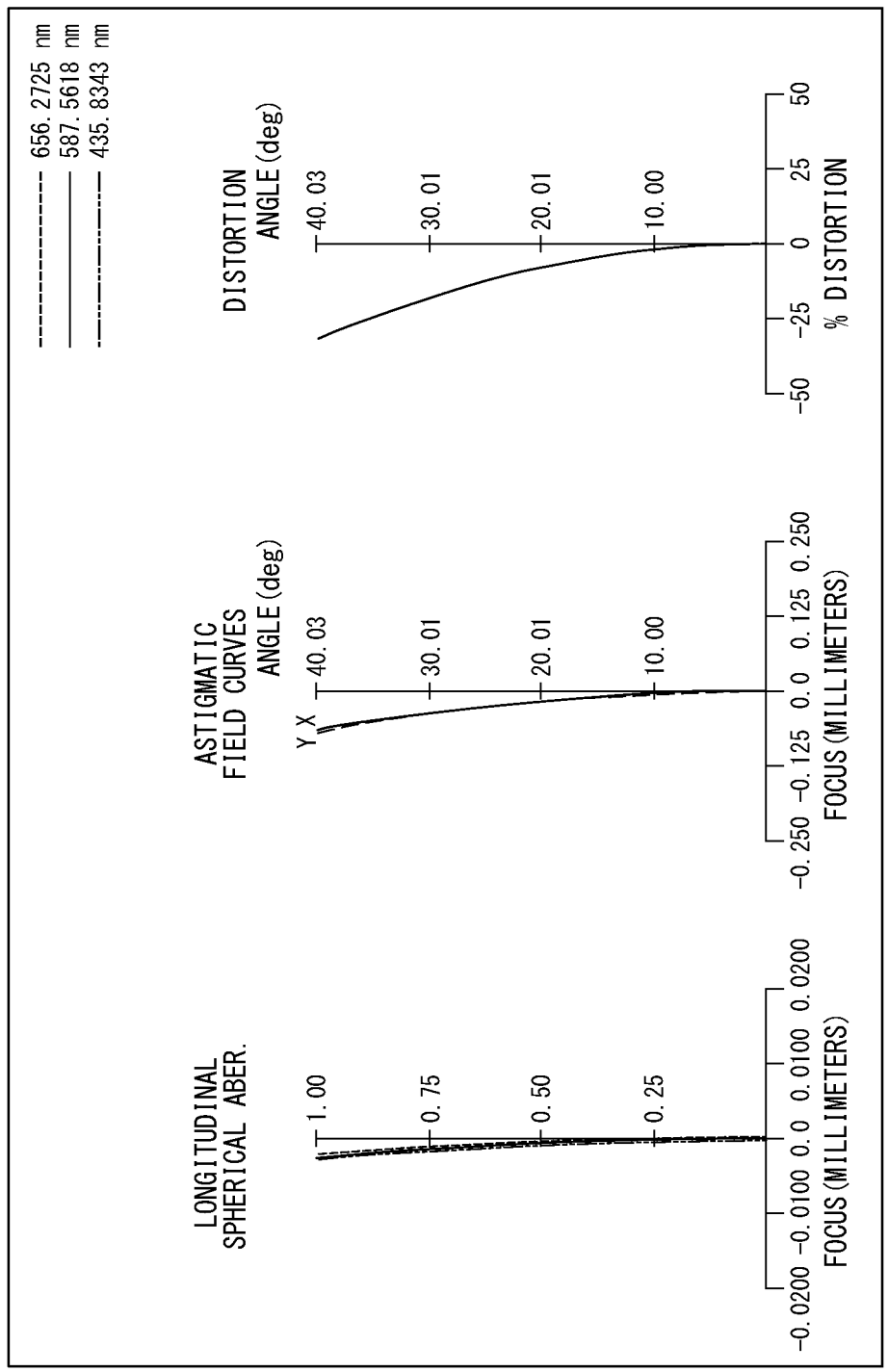
FIG. 13 is an aberration diagram of the objective optical system shown in FIG. 12.

FIG. 13 shows an aberration diagram of the objective optical system of this Example.

| Lens data | | | | |
|---|---|---|---|---|
| Surface number | r | d | Nd | vd |
| OBJ | ∞ | 10 | | |
| 1 | ∞ | 0.1 | 1.561 | 35.4683 |
| 2 | 0.5 | 1.0 | 1.5168 | 64.1673 |
| 3 | −0.5 | 0.0 | | |
| 4 | ∞ | 0.1 | | |
| 5 | 0.5 | 1.0 | 1.5168 | 64.1673 |
| 6 | −0.5 | 0.1 | 1.561 | 35.4683 |
| 7 | ∞ | 1000 | | |
| 8S | ∞ | −1000 | | |
| 9 | ∞ | −0.2168 | | |
| IMG | ∞ | 0.0 | | |

| Miscellaneous data | |
|---|---|
| Numerical aperture at image side | 0.1 |
| Focal length | 0.49 mm |
| Magnification | −0.048 |
| Half angle of view | 40.0° |
| Image height | 0.28 mm |

Example 4

Figure 14:
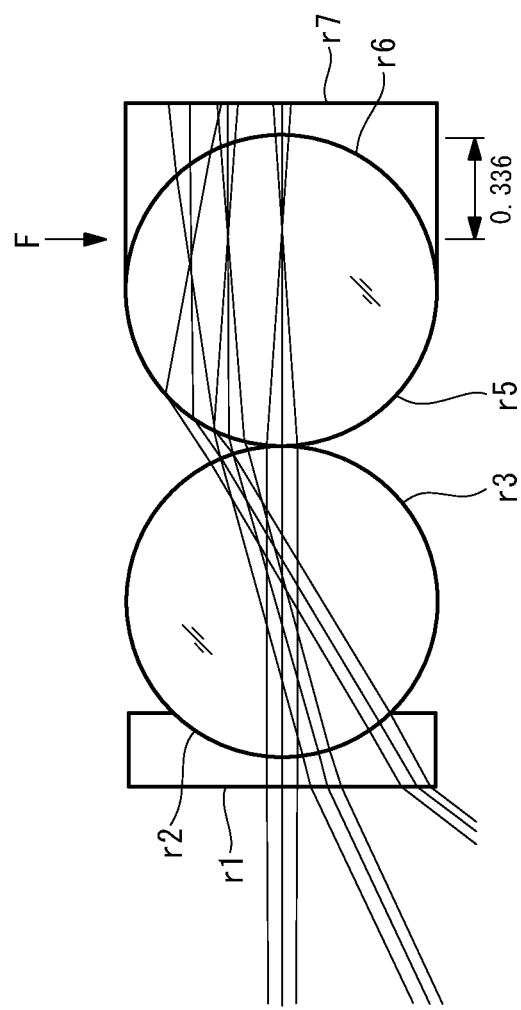
FIG. 14 is a view of the overall configuration of an objective optical system according to Example 4.

FIG. 14 shows the configuration of an objective optical system according to Example 4 of the present invention. The objective optical system of this Example is composed of a first spherical lens, a second spherical lens, a first optical medium, a second optical medium, and an aperture diaphragm. In FIG. 14, the aperture diaphragm is not shown.

The first spherical lens and the second spherical lens have the same radius and are made of the same material. The first spherical lens and the second spherical lens are in contact with each other at one point on the optical axis. The object-side surface of the first optical medium is a flat surface perpendicular to the optical axis. The back focal point F is located inside the second spherical lens. Specifically, the value of the middle part of the inequality of conditional expression (1') is 1.52, and the objective optical system of this Example satisfies conditional expression (1'). The distance between the back focal point F and the opposite lens surface of the second spherical lens from the object is 0.336 mm.

Figure 15:
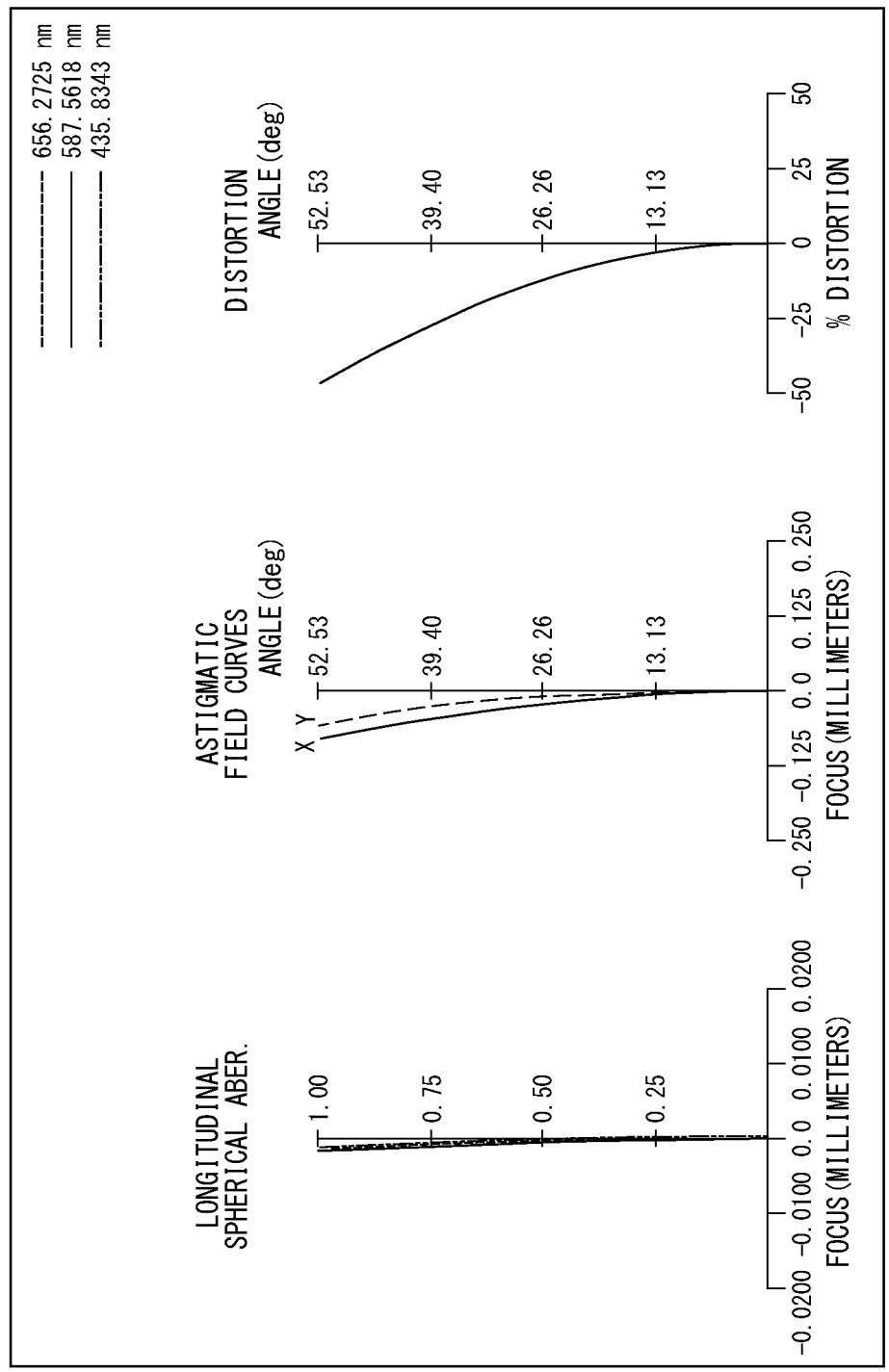
FIG. 15 is an aberration diagram of the objective optical system shown in FIG. 14.

FIG. 15 shows an aberration diagram of the objective optical system of this Example.

| Lens data | | | | |
|---|---|---|---|---|
| Surface number | r | d | Nd | vd |
| OBJ | ∞ | 10 | | |
| 1 | ∞ | 0.1 | 1.561 | 35.4683 |
| 2 | 0.5 | 1.0 | 1.58913 | 61.13 |
| 3 | −0.5 | 0.0 | | |
| 4 | ∞ | 0.0 | | |
| 5 | 0.5 | 1.0 | 1.58913 | 61.13 |
| 6 | −0.5 | 0.1 | 1.561 | 35.4683 |
| 7 | ∞ | 1000 | | |
| 8S | ∞ | −1000 | | |
| 9 | ∞ | −0.2635 | | |
| IMG | ∞ | 0.0 | | |

| Miscellaneous data | |
|---|---|
| Numerical aperture at image side | 0.1 |
| Focal length | 0.43 mm |
| Magnification | −0.042 |
| Half angle of view | 52.5° |
| Image height | 0.3025 mm |

Example 5

Figure 16:
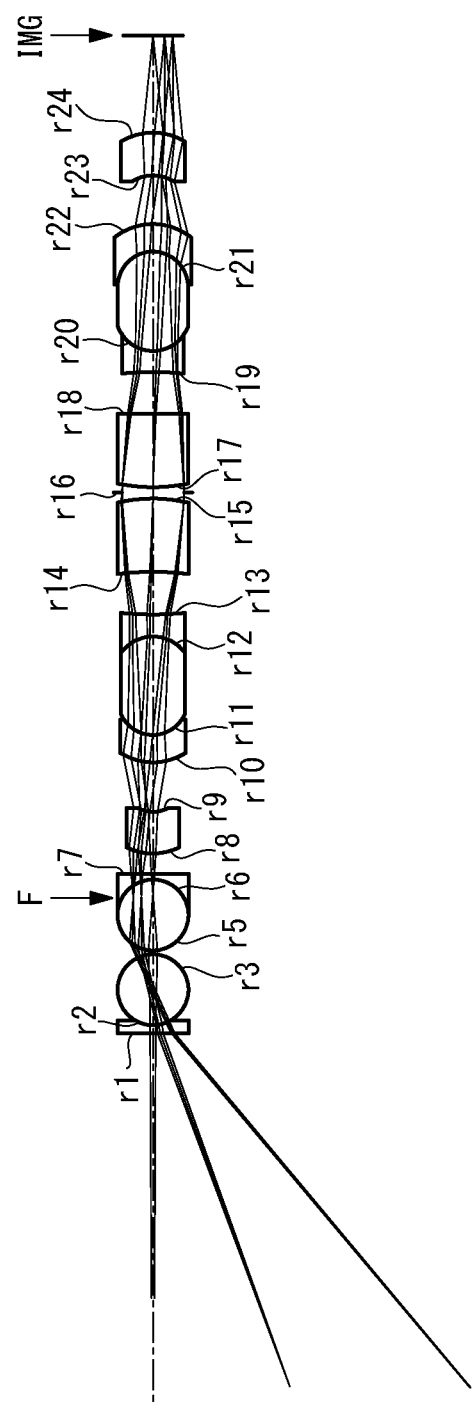
FIG. 16 is a view of the overall configuration of an objective optical system according to Example 5.

FIG. 16 shows the configuration of an objective optical system according to Example 5 of the present invention. The objective optical system of this Example is an example obtained by combining an image transmission system that is formed of a combination of a plurality of lenses, with the objective optical system of Example 4. An aperture diaphragm is disposed inside the image transmission system.

| Lens data | | | | |
|---|---|---|---|---|
| Surface number | r | d | Nd | vd |
| OBJ | ∞ | 10 | | |
| 1 | ∞ | 0.2 | 1.561 | 35.4683 |
| 2 | 1.0 | 2.0 | 1.58913 | 61.13 |
| 3 | −1.0 | 0.0 | | |
| 4 | ∞ | 0.1 | | |
| 5 | 1.0 | 2.0 | 1.58913 | 61.13 |
| 6 | −1.0 | 0.2 | 1.561 | 35.4683 |
| 7 | ∞ | 0.56 | | |
| 8 | 1.8288 | 1.1653 | 1.9020 | 25.1014 |
| 9 | 1.1556 | 1.4021 | | |
| 10 | 1.6464 | 0.7648 | 1.84139 | 24.5591 |
| 11 | 0.9995 | 2.8012 | 1.5588 | 62.5585 |
| 12 | −1.0476 | 0.5968 | 1.647689 | 33.8482 |
| 13 | 6.9284 | 1.1787 | | |
| 14 | −115.428 | 2.07 | 1.71736 | 29.6201 |
| 15 | −4.1677 | 0.1718 | | |
| 16S | ∞ | 0.1718 | | |
| 17 | 4.1677 | 2.07 | 1.71736 | 29.6201 |
| 18 | 115.4278 | 1.1787 | | |
| 19 | −6.9284 | 0.5968 | 1.647689 | 33.8482 |
| 20 | 1.0476 | 2.8012 | 1.5588 | 62.5585 |
| 21 | −0.9995 | 0.7648 | 1.84139 | 24.5591 |
| 22 | −1.6464 | 1.4021 | | |
| 23 | −1.1556 | 1.1653 | 1.902 | 25.1014 |
| 24 | −1.8288 | 1.8521 | | |
| 25 | ∞ | 0.9392 | | |
| IMG | ∞ | 0.0 | | |

| Miscellaneous data | |
|---|---|
| Numerical aperture at image side | 0.1 |
| Focal length | 0.45 mm |
| Magnification | 0.092 |

-continued

| Miscellaneous data | |
|---|---|
| Half angle of view | 40.0° |
| Image height | 0.5562 mm |

Example 6

Figure 17:
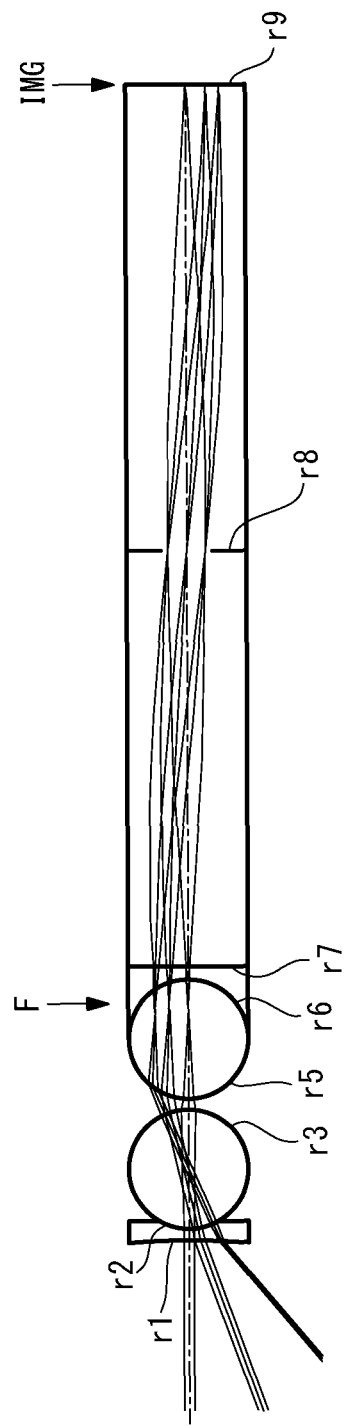
FIG. 17 is a view of the overall configuration of an objective optical system according to Example 6.

FIG. 17 shows the configuration of an objective optical system according to Example 6 of the present invention. The objective optical system of this Example is an example obtained by combining an image transmission system that is formed of a GRIN lens, with the objective optical system of Example 2. An aperture diaphragm is disposed inside the image transmission system.

| Lens data | | | | |
|---|---|---|---|---|
| Surface number | r | d | Nd | vd |
| OBJ | ∞ | 10 | | |
| 1 | −7.61988 | 0.1 | 1.561 | 35.4683 |
| 2 | 0.5 | 1.0 | 1.5168 | 64.1673 |
| 3 | −0.5 | 0.0 | | |
| 4 | ∞ | 0.1 | | |
| 5 | 0.5 | 1.0 | 1.5168 | 64.1673 |
| 6 | −0.5 | 0.1 | 1.561 | 35.4683 |
| 7 | ∞ | 3.5736 | | |
| 8S | ∞ | 3.87 | | |
| 9 | ∞ | 0.0 | | |
| IMG | ∞ | 0.0 | | |

| Miscellaneous data | |
|---|---|
| Numerical aperture at image side | 0.1 |
| Focal length | 0.48 mm |
| Magnification | 0.047 |
| Half angle of view | 40.0° |
| Image height | 0.28 mm |

Example 7

Figure 18:
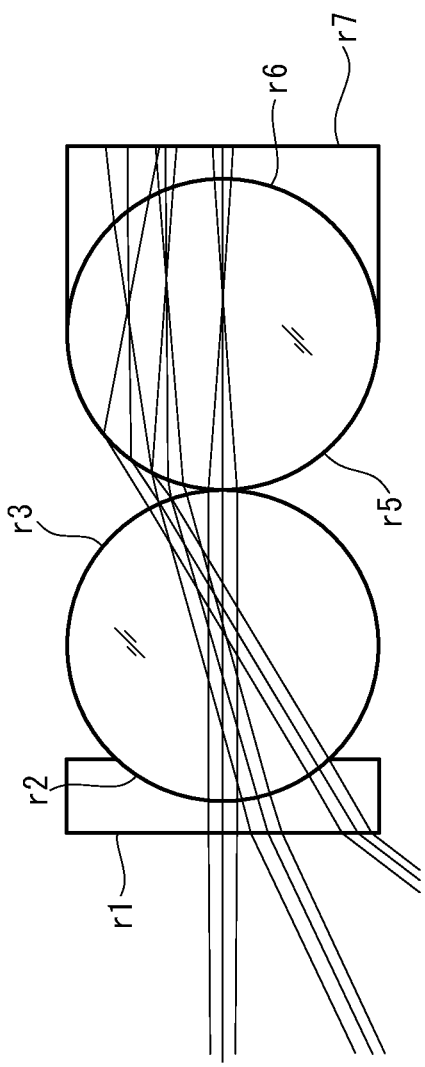
FIG. 18 is a view of the overall configuration of an objective optical system according to Example 7.

FIG. 18 shows the configuration of an objective optical system according to Example 7 of the present invention. The objective optical system of this Example is composed of a first spherical lens, a second spherical lens, a first optical medium, a second optical medium, and an aperture diaphragm. An image transmission system may be further provided at the opposite side of the second optical medium from the object. The image-side surface of the second optical medium is a flat surface perpendicular to the optical axis. In the objective optical system of this Example, because L=0, conditional expression (2) is satisfied.

Figure 19:
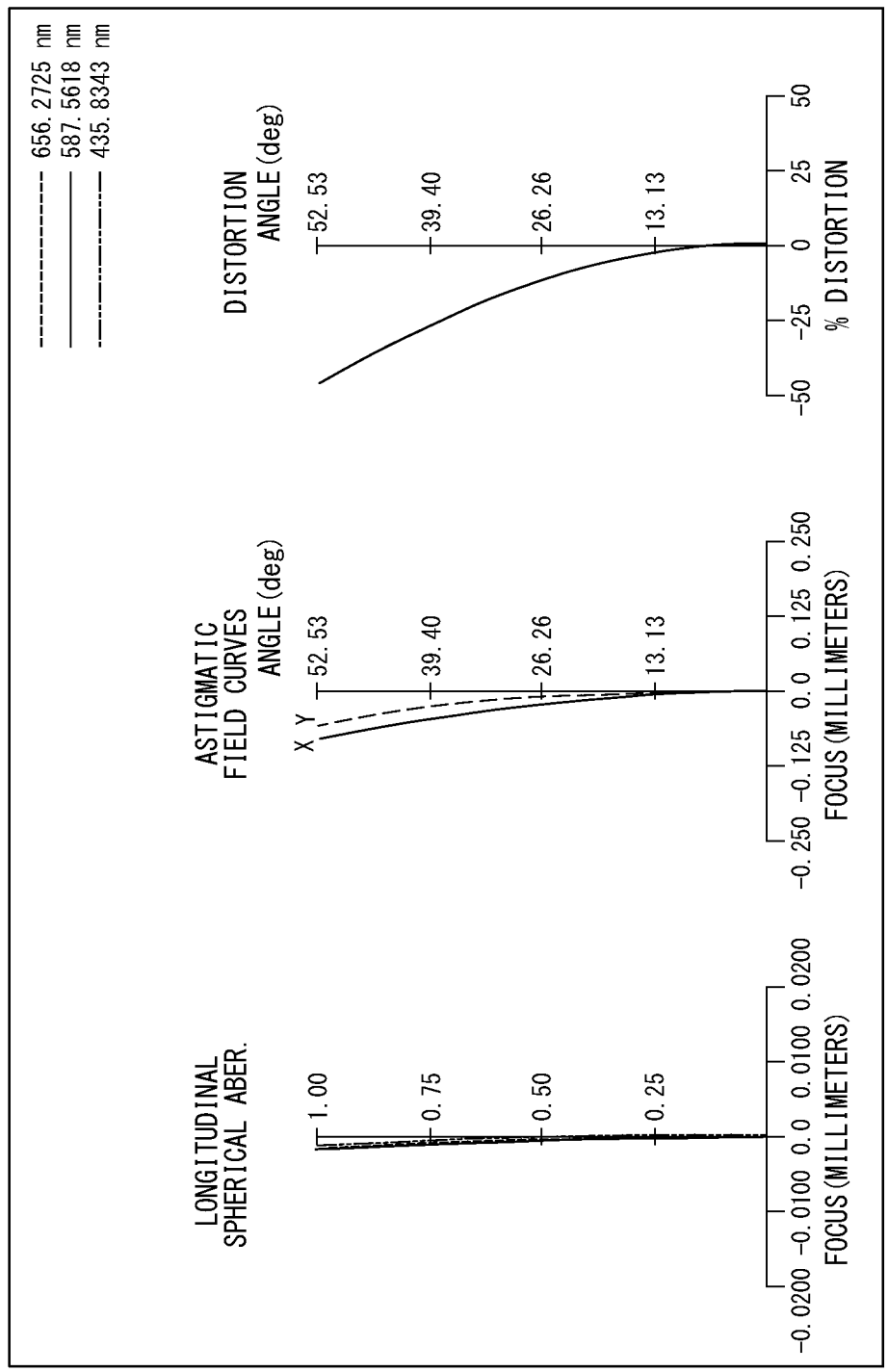
FIG. 19 is an aberration diagram of the objective optical system shown in FIG. 18.

FIG. 19 shows an aberration diagram of the objective optical system of this Example.

| Lens data | | | | |
|---|---|---|---|---|
| Surface number | r | d | Nd | vd |
| OBJ | ∞ | 10.0 | | |
| 1 | ∞ | 0.1 | 1.561 | 35.4683 |
| 2 | 0.5 | 1.0 | 1.58913 | 61.13 |
| 3 | −0.5 | 0.0 | | |

-continued

| Lens data | | | | |
|---|---|---|---|---|
| Surface number | r | d | Nd | vd |
| 4 | ∞ | 0.0 | | |
| 5 | 0.5 | 1.0 | 1.58913 | 61.13 |
| 6 | −00.5 | 0.1 | 1.561 | 35.4683 |
| 7 | ∞ | 1000 | | |
| 8S | ∞ | −1000 | | |
| 9 | ∞ | −0.2635 | | |
| IMG | ∞ | 0.0 | | |

| Miscellaneous data | |
|---|---|
| Numerical aperture at image side | 0.1 |
| Focal length | 0.43 mm |
| Magnification | −0.042 |
| Half angle of view | 52.5° |
| Image height | 0.3025 mm |

The above-described embodiment also leads to the following aspects.

According to one aspect, the present invention provides an objective optical system including: a first spherical lens and a second spherical lens that are arrayed in this order from an object; and at least one of a first optical medium and a second optical medium, wherein the first optical medium is a solid or liquid disposed at an object side of the first spherical lens and is in close contact with a surface on the object side of the first spherical lens, over an entire optical path; the second optical medium is a solid or liquid disposed at an opposite side of the second spherical lens from the object and is in close contact with a surface on the opposite side of the second spherical lens from the object, over the entire optical path; and the optical path between the first spherical lens and the second spherical lens is filled with air.

REFERENCE SIGNS LIST 10, 11 objective optical system
1 first spherical lens
2 second spherical lens
3 first optical medium
4 second optical medium
5 image transmission system
6 aperture diaphragm
G1 first group
G2 second group
A optical axis
F back focal point
I image
O object

The invention claimed is:
1. An objective optical system comprising:
a first spherical lens and a second spherical lens that are arrayed in this order from an object; and
at least one of a first optical medium and a second optical medium,
wherein the first optical medium is a solid or liquid disposed at an object side of the first spherical lens and is in close contact with a surface on the object side of the first spherical lens, over an entire optical path; and
the second optical medium is a solid or liquid disposed at an opposite side of the second spherical lens from the object and is in close contact with a surface on the opposite side of the second spherical lens from the object, over the entire optical path; and wherein a back focal point is located at the opposite side, from the object, of a surface on the object side of the second spherical lens; and an image transmission system that is disposed at the opposite side of the second spherical lens from the object, wherein the back focal point is located inside the second spherical lens.

2. The objective optical system according to claim 1, wherein the first spherical lens and the second spherical lens have radii identical to each other and are made of materials identical to each other; a surface on the object side of the first optical medium is a flat surface perpendicular to the optical axis; and the following conditional expression (1) is satisfied:

$$0 \leq \{n_1(2n_3-n_1)-n_1LN\}/\{2n_3-(n_1-3n_3)(n_1-2)-(n_1-1)LN\} \leq 2 \quad (1)$$

where $n_1$ indicates a refractive index of the first spherical lens and the second spherical lens, $R_1$ indicates a radius of the first spherical lens and the second spherical lens, $n_3$ indicates a refractive index of the first optical medium, $L$ indicates the interval on the optical axis between a surface on the opposite side of the first spherical lens from the object and the surface on the object side of the second spherical lens, and $N=(n_1n_3+n_1-2n_3)/R_1$.

3. The objective optical system according to claim 1, wherein a surface on the opposite side of the second optical medium from the object is a flat surface perpendicular to the optical axis; and the following conditional expression (2) is satisfied:

$$1 \leq (R_1+R_2)*[\{1/\cos(2\theta_2-\theta_1)\}-1]/L \quad (2)$$

where $R_1$ indicates a radius of the first spherical lens, $R_2$ indicates a radius of the second spherical lens, $L$ indicates the interval on the optical axis between a surface on the opposite side of the first spherical lens from the object and the surface on the object side of the second spherical lens, $n_2$ indicates a refractive index of the second spherical lens, $n_4$ indicates a refractive index of the second optical medium, $\theta_1=\sin^{-1}(1/n_4)$, and $\theta_2=\sin^{-1}(1/n_2)$.

4. The objective optical system according to claim 1, further comprising an aperture diaphragm, wherein the aperture diaphragm is disposed at the opposite side of the second spherical lens from the object.

5. The objective optical system according to claim 1, wherein an optical path between the first spherical lens and the second spherical lens is filled with air.

6. An endoscope comprising the objective optical system according to claim 1.

7. The objective optical system according to claim 1, wherein the second and third regions oppose each other in an optical axis direction.

8. The objective optical system according to claim 7, wherein the objective optical system comprises each of the first optical medium and the second optical medium.

9. The objective optical system according to claim 1, wherein the first optical medium is a solid.

10. The objective optical system according to claim 1, wherein the second optical medium is a solid.

11. The objective optical system according to claim 1, wherein the first optical medium is a liquid.

12. The objective optical system according to claim 1, wherein the second optical medium is a liquid.

13. An objective optical system comprising:

a first spherical lens and a second spherical lens that are arrayed in this order from an object; and at least one of a first optical medium and a second optical medium;

an image transmission system that is disposed at the opposite side of the second spherical lens from the object, wherein the first optical medium is a solid or liquid disposed at an object side of the first spherical lens and is in close contact with a surface on the object side of the first spherical lens, over an entire optical path; and the second optical medium is a solid or liquid disposed at an opposite side of the second spherical lens from the object and is in close contact with a surface on the opposite side of the second spherical lens from the object, over the entire optical path;

a back focal point is located at the opposite side, from the object, of a surface on the object side of the second spherical lens;

the back focal point is located inside the second spherical lens;

the first spherical lens and the second spherical lens have radii identical to each other and are made of materials identical to each other;

a surface on the object side of the first optical medium is a flat surface perpendicular to the optical axis; and the following conditional expression (1) is satisfied:

$$0 \leq \{n_1(2n_3-n_1)-n_1LN\}/\{2n_3-(n_1-3n_3)(n_1-2)-(n_1-1)LN\} \leq 2 \quad (1)$$

where $n_1$ indicates a refractive index of the first spherical lens and the second spherical lens, $R_1$ indicates a radius of the first spherical lens and the second spherical lens, $n_3$ indicates a refractive index of the first optical medium, $L$ indicates the interval on the optical axis between a surface on the opposite side of the first spherical lens from the object and the surface on the object side of the second spherical lens, and $N=(n_1n_3+n_1-2n_3)/R_1$.

14. The objective optical system according to claim 13, further comprising an aperture diaphragm, wherein the aperture diaphragm is disposed adjacent the fourth region of the second spherical lens.

15. The objective optical system according to claim 13, wherein an optical path between the first spherical lens and the second spherical lens is filled with air.

16. An objective optical system comprising:

a first spherical lens and a second spherical lens that are arrayed in this order from an object; and at least one of a first optical medium and a second optical medium;

an image transmission system that is disposed at the opposite side of the second spherical lens from the object, wherein the first optical medium is a solid or liquid disposed at an object side of the first spherical lens and is in close contact with a surface on the object side of the first spherical lens, over an entire optical path; and the second optical medium is a solid or liquid disposed at an opposite side of the second spherical lens from the object and is in close contact with a surface on the opposite side of the second spherical lens from the object, over the entire optical path;

a back focal point is located at the opposite side, from the object, of a surface on the object side of the second spherical lens;

the back focal point is located inside the second spherical lens;

a surface on the opposite side of the second optical medium from the object is a flat surface perpendicular to the optical axis; and the following conditional expression (2) is satisfied:

$$1 \leq (R_1+R_2)*[\{1/\cos(2\theta_2-\theta_1)\}-1]/L \qquad (2)$$

where $R_1$ indicates a radius of the first spherical lens, $R_2$ indicates a radius of the second spherical lens, L indicates the interval on the optical axis between a surface on the opposite side of the first spherical lens from the object and the surface on the object side of the second spherical lens, $n_2$ indicates a refractive index of the second spherical lens, $n_4$ indicates a refractive index of the second optical medium, $\theta_1 = \sin^{-1}(1/n_4)$, and $\theta_2 = \sin^{-1}(1/n_2)$.

17. The objective optical system according to claim 16, further comprising an aperture diaphragm, wherein the aperture diaphragm is disposed adjacent the fourth region of the second spherical lens.

18. The objective optical system according to claim 16, wherein an optical path between the first spherical lens and the second spherical lens is filled with air.

* * * * *